United States Patent
Rodriguez et al.

(10) Patent No.: US 6,228,652 B1
(45) Date of Patent: May 8, 2001

(54) METHOD AND APPARATUS FOR ANALYZING CELLS IN A WHOLE BLOOD SAMPLE

(75) Inventors: Carlos M. Rodriguez; Jose M. Cano; Barbara Carrillo, all of Miami; Kristie M. Gordon, Coral Gables; Allan F. Horton, Miami; Ronald D. Paul, Fort Lauderdale; Mark A. Wells, Davie; James L. Wyatt, Plantation, all of FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/251,019

(22) Filed: Feb. 16, 1999

(51) Int. Cl.[7] .................................................. G01N 33/48
(52) U.S. Cl. .................................. 436/63; 436/8; 436/10; 436/17; 436/18; 436/66; 436/172; 436/164; 436/165; 435/2; 435/808; 422/73; 422/82.01; 422/82.02; 422/82.05; 422/82.08; 422/82.09; 356/39; 356/73; 356/335; 356/336
(58) Field of Search ................................ 436/8, 10, 17, 436/18, 63, 66, 164, 165, 172, 174, 175, 179, 805; 435/2, 808; 422/73, 82.01, 82.02, 82.05, 82.08, 82.09; 356/39, 73, 335, 336

(56) References Cited

U.S. PATENT DOCUMENTS

| | | | |
|---|---|---|---|
| 4,445,391 | 5/1984 | Cabrera | 73/864.12 |
| 4,507,977 | 4/1985 | Cabrera | 73/864.12 |
| 4,673,288 | * 6/1987 | Thomas et al. | 356/72 |
| 4,702,889 | 10/1987 | Cabrera et al. | 422/103 |
| 5,079,959 | 1/1992 | Miyake et al. | 73/864.85 |
| 5,106,187 | * 4/1992 | Bezanson | 356/73 |
| 5,125,737 | 6/1992 | Rodriguez et al. | 365/39 |
| 5,255,568 | 10/1993 | Del Valle et al. | 73/863 |
| 5,492,833 | * 2/1996 | Rodriguez et al. | 436/63 |
| 5,631,165 | 5/1997 | Chupp et al. | 436/43 |
| 5,639,666 | * 6/1997 | Shenkin | 436/63 |
| 5,656,499 | 8/1997 | Chupp et al. | 436/43 |
| 5,798,827 | * 8/1998 | Frank et al. | 356/39 |
| 6,060,322 | * 5/2000 | Horton et al. | 436/63 |

OTHER PUBLICATIONS

Hudson et al. *Cytometry*, vol. 22, pp. 150–153, 1995.*
Leif et al. *Clinical Chemistry*, vol. 23, No. 8, pp. 1492–1498, 1977.*
Thomas, et al., *Journal of Histochemistry and Cytochemistry*, vol. 25, No. 7, pp. 827–835 (1977).

* cited by examiner

Primary Examiner—Maureen M. Wallenhorst
(74) Attorney, Agent, or Firm—Warren W. Kurz; Mitchell E. Alter

(57) ABSTRACT

A blood analyzing instrument includes a single transducer for simultaneously measuring the DC volume, RF conductivity, light scattering and fluorescence characteristics of blood cells passing through a cell-interrogation zone. Preferably, the transducer includes an electro-optical flow cell which defines a cell-interrogation zone having a square transverse cross-section measuring approximately 50×50 microns, and having a length, measured in the direction of cell flow, of approximately 65 microns.

24 Claims, 25 Drawing Sheets

METHOD AND APPARATUS FOR ANALYZING CELLS IN A WHOLE BLOOD SAMPLE

BACKGROUND OF THE INVENTION

1. Field of the Invention

This invention relates to improvements in methods and apparatus for differentiating and enumerating the various constituent subpopulations or types of cells in a whole blood sample.

2. Discussion of the Prior Art

In diagnosing different illnesses and disease states, it is common to analyze a patient's peripheral blood to differentiate and enumerate the various types of constituent blood cells and platelets, as well as to determine certain parameters or characteristics thereof. The respective concentrations and relative percentages of the different types of blood cells are highly indicative of certain diseases and the extent to which such diseases have spread. In general, a sample of whole blood comprises various types of cells, both blood cells and non-blood cells (e.g., tumor cells, bacteria, etc.) suspended in a liquid medium or plasma. The blood cells are three basic types, namely, red cells (erythrocytes), white cells (leukocytes), and platelets. Depending on the level of maturity, red cells are often further classified into three subsets, namely, nucleated red blood cells (NRBC's), reticulated red cells ("retics"), and mature red blood cells (RBC's). Mature white cells, on the other hand, fall into one of five different subsets, namely, monocytes, lymphocytes, eosinophils, neutrophils and basophils. Each of the white cell subsets can be further classified into subclasses based on their respective level of maturity, activation or abnormality. Typically, the number of red cells outnumber the total number of white cells by about 1000:1. Platelets, which are of interest at least from the standpoint that they control the ability of the blood to clot, are of three general types, mature platelets, reticulated platelets and large platelets.

In addition to determining the respective concentrations and relative percents of each of the above cell types and subsets, a thorough analysis of a blood sample will also provide information regarding various blood parameters and cell characteristics including, for example, the hemoglobin (Hgb) concentration, hematocrit value (Hct), mean cell volume (MCV), the total number of red and white cells and platelets per unit volume, the distribution width of red cells (RDW) and platelets (PDW), etc.

The detection and enumeration of most of the above cell types, as well as a determination of the above cell parameters, can be accomplished by using any one of several commercially available hematology instruments. Such instruments include Beckman Coulter's GEN●S™, STKS™, and MAXM™ Hematology Instruments; Abbott Laboratories' Cell Dyne 3000/4000 Hematology Instruments; and Toa's Sysmex Series of Hematology Instruments. In automatically acquiring data on each cell type, all of the above-mentioned hematology instruments use at least two discrete cell-analyzing transducers. One (or more) of these transducers operates to acquires data useful in differentiating and enumerating the five different types of white cells, and another transducer is dedicated to counting and sizing of red cells, white cells and platelets in a precise volume of sample. The respective outputs of the multiple transducers are processed by a central processing unit to provide an integrated cell analysis report. In the Beckman Coulter instruments, an electro-optical flow cell (transducer) produces signals indicative of the respective volume (V), electrical conductivity (C) and light scattering (S) properties of each white cell passing therethrough to provide a "five-part differential" of the five white cell types. Additional transducers operate on the well known Coulter Principle, one serving to count red cells and platelets in a highly diluted sample, and others serve to count white cells in a lysed sample. Information from the three transducers is processed and, in some cases, correlated (e.g., by multiplying the relative percentage of each white cell subset, as obtained from the electro-optical flow cell, by the absolute number of white cells counted by the Coulter transducer) to provide information about each cell type or subset, e.g., the concentration (number per unit volume) of each white cell subset in the whole blood sample being analyzed. In the Abbott instruments, the five-part diff information is provided by an optical flow cell that detects only light scatter and light polarization information. Here, again, a pair of additional transducers operating on the Coulter Principle serves to size and count white cells, red cells and platelets. The respective outputs of the two transducers are correlated with each other to report information on different cell types and subsets. In the Toa instruments, the five-part differential information is provided by a pair of electrical flow cells (Coulter transducers) that measure only the cell's DC volume and RF conductivity. Different lysing reagents are used to differentially process two or more aliquots of the blood sample, prior to passage through the two transducers. A third Coulter transducer operates to detect and count red cells and platelets. As in the Beckman Coulter and Abbott instruments, the respective outputs of the several transducers are correlated to provide the five-part differential information.

As indicated above, conventional hematology instruments, while being capable of differentiating and enumerating the vast majority of cell types and subsets in a peripheral blood sample, cannot readily differentiate all subsets of cells, particularly those that are abnormal or immature. An "extended differential" measurement by which these abnormal and immature cells may be detected and counted can be made manually by first producing a blood-smear of a sample of interest on a glass microscope slide, staining the smear with a dye to enable the cells to be visualized, whereby abnormal or immature cells of interest can be visually differentiated from other cells, and then examining the resulting stained blood-smear under a microscope. Alternatively, some blood types of an extended differential measurement can be detected using a conventional flow cytometer. In such an instrument, a blood sample that has been previously prepared, e.g., by either (1) mixing the sample with fluorochrome-labeled monoclonal antibodies or the like which serve to selectively "tag" certain cells of interest, or (2) mixing the sample with a fluorescent stain adapted to selectively mark cells of interest, is passed through an optical flow cell. As each cell in the sample passes through the flow cell, it is irradiated with a beam of photons adapted to excite the fluorescent material associated with the cells of interest. Fluorescent radiation emitted by each of the labeled cells, together with radiation scattered by each cell is detected and used to differentiated the cells of interest from other cells in the sample. Commercial, stand-alone, flow cytometers are made by Beckman Coulter, Toa Medical Electronics, Cytomation, Bio-Rad, and Becton Dickinson. It is known in the prior art to integrate flow cytometers and hematology instruments into a single automated laboratory system in which blood samples are automatically advanced along a track past these different instruments. As sample-containing vials pass each instrument, a blood sample is aspirated from each vial and analyzed by the instrument. Instrument systems combining discrete hematology and flow cytometry instruments are commercially available from Beckman Coulter and Toa Medical Electronics, reference being made to Toa's HST Series.

In U.S. Pat. Nos. 5,631,165 and 5,565,499, an attempt is made to fully integrate the respective functions of hematology and flow cytometry instruments into a single instrument. Such an instrument comprises a plurality of transducers, including an optical flow cell adapted to make fluorescence and multiangle light scatter measurements, an electrical impedance-measuring transducer (a Coulter transducer), and a colorimeter for measuring the overall hemoglobin content of a blood sample. The respective outputs from these transducers are processed and correlated to produce a report on red, white and fluorescent cells.

As suggested above, the requirement to correlate the respective outputs of multiple transducers in order to report certain characteristics of a cell type or subset can, under certain circumstances, be problematic in that it introduces an uncertainty in the analytical results. The validity of the requisite correlation step presupposes that the sample processed by one transducer is identical in content to that processed by the other transducer(s). This may not always be the case. Ideally, all of the measurements made on a cell should be made simultaneously by the same transducer. In such a case, there would be no need to correlate data from independent or separate transducers. Further, the simultaneous measurement of multiple parameters on a single cell using a single transducer enables a multidimensional cell analysis that would not be possible using separate transducers, or even using a single transducer when the parameter measurements are spatially separated in time.

The desirability of using a single electro-optical transducer to simultaneously measure the volume (V), conductivity (C), light scatter (S) and fluorescence (F) of a single cell has been suggested in the prior art. As noted above, such a transducer offers the advantage of making all measurements simultaneously on the same cell, rather than making some measurements on one cell with one transducer, making other measurements on another cell of the same type using another transducer, and then attempting to correlate the results from the two transducers to draw certain conclusions about the cell sample. In a disclosure by Thomas et al., Journal of Histochemistry and Cytochemistry, Vol. 25, No. 7, pp. 827–835 (1977), an automated multiparameter analyzer for cells (AMAC) is proposed. Such an analyzer comprises a single transducer adapted to simultaneously measure four different cell characteristic, namely, the above-noted V,C,S and F characteristics. In the Thomas et al. article, two different electro-optical flow cells are disclosed, one flow cell (the AMAC III) having a flow passageway of square transverse cross-section, measuring 100 microns on each side, and the other flow cell (AMAC IV) having a circular transverse cross-section. While the AMAC IV flow cell affords certain advantages in terms of manufacturability, the AMAC III flow cell was preferred due to its flat face geometry and its inherent ability to reduce optical aberrations, thereby better enabling the beam of excitation radiation to be focused on the cell path, and better enabling cell fluorescence to be coupled to a photo-detector. Though proposed for making simultaneous measurements of V, C, S and F, there is no evidence that either the AMAC III or IV flow cells was ever used for making such measurements. In the Thomas et al. article, for example, it is noted that an RF measurement (which is used in determining the "opacity" parameter) conducted on beads passing through the AMAC III flow cell gave rise to imprecise results. These results were attributable to a signal-to-noise problem associated with the relatively large cross sectional area (100×100 microns) of the flow cell. Further, it is apparent that light scattering measurements were never conducted using the AMAC flow cells. Thus, though others have proposed a single VCSF transducer for making simultaneous measurements on each cell, no one has either reduced such a concept to practice or has provided a technically enabling disclosure for doing so.

SUMMARY OF THE INVENTION

In view of the foregoing discussion, a primary object of this invention is to provide an automated instrument by which all of the aforementioned cell characteristics, i.e., DC volume, RF conductivity (opacity), light scatter and fluorescence characteristics, can be determined simultaneously, whereby any need to correlate data gathered from separate transducers is obviated.

Another object of this invention is to provide an improved automated method for analyzing cells in a whole blood sample, a method that is improved from the standpoint that there is no need to correlate data obtained from multiple and separate transducers in order to derive certain information about a cell subset of interest.

Another object of this invention is to provide an improved flow cell apparatus for enumerating blood cell types in a whole blood sample.

In accordance with one aspect of the invention, a preferred instrument for differentiating and determining the respective concentrations of various types of cells in a whole blood sample generally comprises the following elements in combination:

(a) a single flow cell defining a cell-interrogation zone through which blood cells can be made to flow seriatim;

(b) means for aspirating a sample of whole blood from a container;

(c) means for dispensing at least a first aliquot of the aspirated whole blood sample;

(d) means for subjecting the first aliquot of whole blood to a lysing reagent to provide a lysed sample containing predominantly white blood cells and nucleated red blood cells;

(e) means for subjecting one or more subsets of cells contained in the lysed samples to a fluorescent material, thereby causing said subsets of cells to become labeled with such fluorescent material;

(f) metering means for dispensing a metered volume of the lysed sample;

(g) means for causing said metered volume of said lysed sample to flow through the cell-interrogation zone of the flow cell so that blood cells in said metered volume flow through said cell-interrogation zone seriatim;

(h) circuit means for (a) simultaneously establishing DC and RF current flows through said cell-interrogation zone while blood cells are flowing therethrough, each of said blood cells being effective to (i) modulate the DC current in said zone as a finction of the cell's volume, and (ii) modulate the RF current flow in said zone as a finction of the cell's internal conductivity; and (b) detecting modulations in said DC and RF currents;

(i) optical means for irradiating individual blood cells flowing through said cell-interrogation zone with a beam of radiation propagating along an axis perpendicular to the direction of sample flow, said radiation being adapted to cause the fluorescent material to fluoresce;

(j) radiation scatter-detecting means for detecting radiation scattered from an irradiated blood cell in said zone, said radiation scatter detecting means being adapted to detect scattered radiation within a plurality of discrete angular ranges measured with respect to said axis;

(k) fluorescence-detecting means for detecting radiation fluorescing from fluorescent material-labeled subset of cells as a result of being irradiated by said optical means; and (l) analyzing means, operatively coupled to said circuit means and to the respective radiation scatter- and fluorescence-detecting means, for differentiating and determining the respective concentrations of different subsets of white cells and fluorescent material-labeled cells.

According to another preferred embodiment, the above-noted dispensing means is effective to dispense a second aliquot of the aspirated whole blood sample, and the apparatus further comprises the following additional elements:

(m) means for subjecting the second aliquot of whole blood to a diluent to provide a diluted sample containing predominantly red blood cells and platelets;

(n) means for subjecting the diluted sample to a fluorescent material, whereby at least one selected subset of red cells or platelets becomes labeled with such fluorescent material; and (o) means for dispensing a metered volume of the diluted sample and causing said metered volume of said diluted sample to flow through the cell-interrogation zone of the flow cell so that blood cells in such metered volume flow through said cell-interrogation zone seriatim. In this embodiment, the analyzing means further operates to differentiate and determine the respective concentrations of different subsets of red blood cells and platelets based on their respective DC volume (V), RF conductivity (C), light scatter (S) and fluorescence (F) properties.

Preferably, the five different subsets of mature white cells are differentiated by analyzing the combination of their respective DC volume (V), RF conductivity (C) and light scattering (S) properties. Other white cell subsets, abnormal cells and immature cells (e.g., NRBC's, blasts, CD4/CD8 positive lymphocytes, immature granulocytes, atypical lymphocytes and stem cells) are differentiated based upon their respective DC volume, RF conductivity, fluorescent label and light scattering properties.

Alternatively, the apparatus of the invention comprises means for differentiating various subsets of red blood cells and platelets by simultaneously determining the V, C, S, and F characteristics of individual cells in such subsets.

According to another aspect of the invention, an automated method for analyzing different cell types and respective subsets thereof in a whole blood sample comprises the steps of:

(a) providing a flow cell apparatus having a single transducer adapted to simultaneously measure the respective DC volume, RF conductivity, light scattering and fluorescent properties of blood cells passing seriatim through an interrogation zone within said transducer;

(b) aspirating a sample of whole blood from a container;

(c) dispensing first and second aliquots of the aspirated whole blood sample;

(d) subjecting said first aliquot of whole blood to a lysing reagent to provide a lysed sample of predominantly white blood cells;

(e) subjecting said second aliquot of whole blood to a diluent to provide a diluted sample;

(f) subjecting one or more subsets of cells contained in the diluted or lysed samples to a fluorescent material, thereby causing said subsets of cells to become labeled with such fluorescent material, said fluorescent material being adapted to fluoresce when exposed to radiation of predetermined wavelength;

(g) dispensing metered volumes of said lysed and diluted samples and causing the respective metered volumes of lysed and diluted samples to flow through said interrogation zone sequentially and so that the respective blood cells in said metered volumes flow through said interrogation zone seriatim;

(h) irradiating individual blood cells flowing through said interrogation zone with a beam of radiation of said wavelength propagating along an axis while establishing DC and RF current flows through said interrogation zone, each of said blood cells being effective, while passing through said interrogation zone, to (i) modulate the DC current in said interrogation zone as a function of the cell's volume, and (ii) modulate the RF current flow in said passageway as a function of the cell's internal conductivity;

(i) detecting modulations in said DC and RF currents while detecting radiation scattered by and fluorescence emitted from an irradiated blood cell in said interrogation zone;

(j) differentiating and counting different types of white cells in said lysed sample based upon each cell's DC volume (V), RF conductivity (C), light scattering (S) and fluorescent (F) properties; and (k) differentiating and counting different types of red blood cells and platelets in said diluted sample based upon each cell's DC volume (V), RF conductivity (C), fluorescent label (F) and light scattering (S) properties.

According to another embodiment of the invention, the above automated method further comprises the steps of (1) dispensing a third aliquot of whole blood and subjecting such third aliquot to a reagent containing fluorochromes conjugated to monoclonal antibodies specific to a selected subset of cells in said third aliquot, whereby said selected subset of cells becomes labeled with such fluorochromes; and (m) differentiating and counting such selected subset based on the V, C, S, and F properties of such subset. Also preferred is that the method of the invention further comprises the step of differentiating and counting nucleated red blood cells, abnormal cells and immature cells in said lysed sample based on the respective V, C, S, F parameters of such cells.

As an alternative to the automated method briefly described above, the steps associated with detecting the V, C, S, F characteristics of the cells in each of the three samples (i.e., the lysed sample, the diluted sample and the labeled sample) can be carried out separately so that, for example, only the white cells are analyzed, or only the red cells and platelets are analyzed, or only the fluorescent cells are analyzed.

According to yet another aspect of the invention, there is provided a novel optical flow cell for simultaneously detecting the V, C, S, and F characteristics of formed bodies, including blood cells and platelets, suspended in a liquid sample. Such a flow cell comprises an optically transparent element in the form of a rectangular prism and defining a passageway through which formed bodies in said sample can be made to pass one at a time. Preferably, a portion of the passageway defines a cell-interrogation zone having a substantially square transverse cross-section (determined perpendicular to the direction of sample flow) of approximately 50 microns on each side and a length of approximately 65 microns, measured in the direction of sample flow. The flow cell supports a pair of electrodes, connectable to a source of electrical energy, for producing a current flow through the flow cell while particles are passing therethrough, and an optical element through which radiation emanating within the cell-interrogation zone can be optically coupled to a photo-detector.

The invention and its many advantages will be better appreciated from the ensuing detailed description of preferred embodiments, reference being made to the accompanying drawings.

DETAILED DESCRIPTION OF PREFERRED EMBODIMENTS

Figure 1:
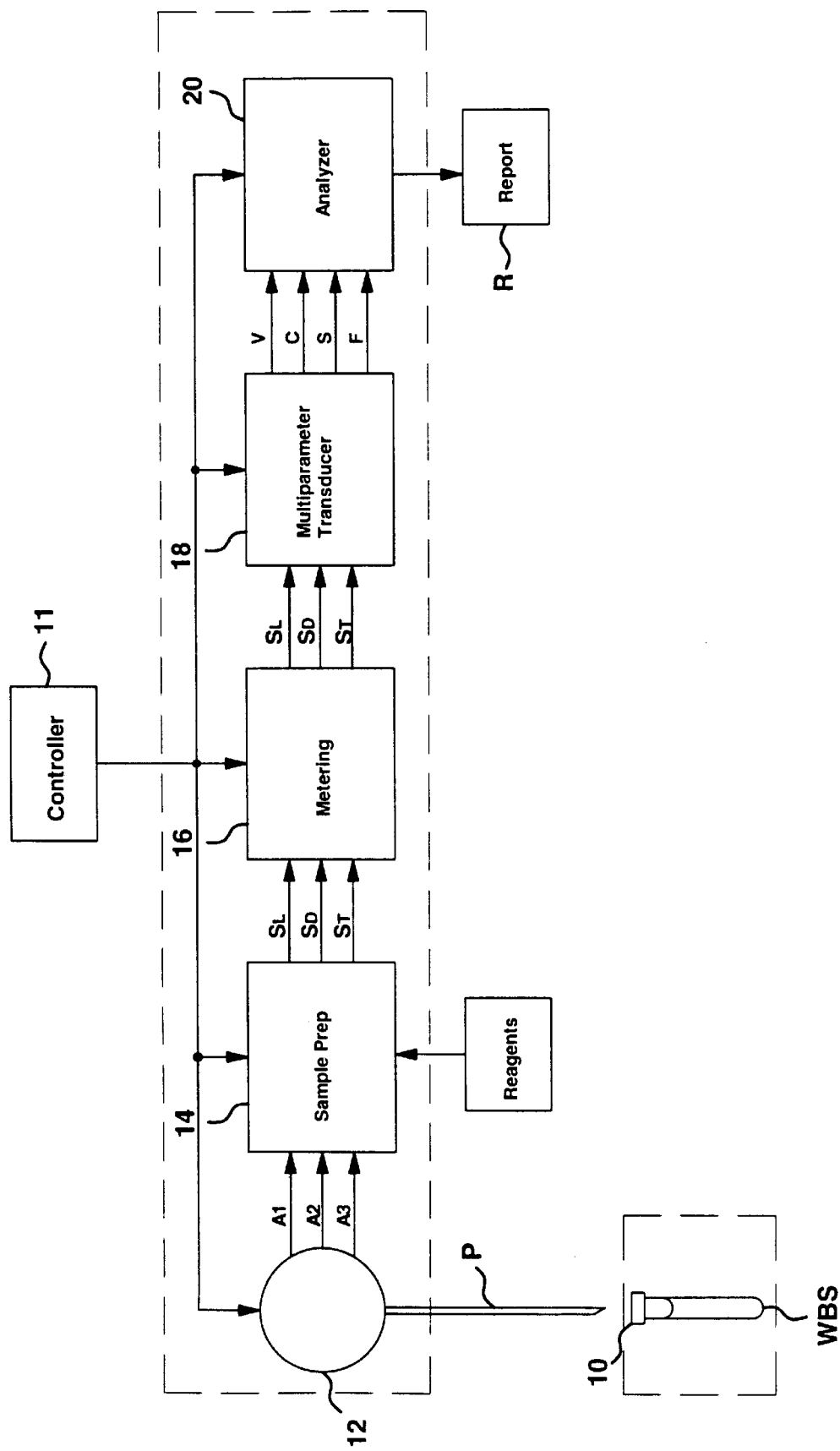
FIG. 1 is a block diagram of a blood cell analyzing instrument embodying the present invention.

Referring now to the drawings, FIG. 1 schematically illustrates an automated cell analyzer CA embodying the present invention. Such analyzer is adapted to aspirate a whole blood sample WBS from a container or vial 10, analyze its cellular make-up, as instructed by a controller 11, and report its findings. One or more vials 10 carried by a sample transporter ST, for example a single tube holder, a sample tray or rack holder, is advanced by a conveyer (not shown) to present the blood sample to an aspiration probe P. The latter is selectively operable to draw a predetermined volume of the blood sample from vial 10 into a conventional blood sampling valve 12 or the like, such as disclosed, for example, in the commonly assigned U.S. Pat. Nos. 5,255,568; 4,702,889; 4,507,977; and 4,445,391. Such valves operate in a known manner to segment the sample into precise aliquots, microliters in volume, for analysis. A plurality of such aliquots, $A_1$, $A_2$, $A_3$, are dispensed to a sample-preparation station 14 at which each aliquot is mixed or otherwise subjected to a reagent adapted to treat selected cells in the sample. According to a preferred embodiment, the sample preparation station can produce, for example, a lysed and stained sample, $S_L$, comprising predominantly white blood cells and other cells (e.g., NRBC's) that been stained with a fluorescent dye; a diluted and stained sample, $S_D$, containing all blood cell types in a highly diluted suspension, some of such cells (e.g., the retic subset) being stained with a fluorescent dye; and a lysed and tagged sample, $S_T$, comprising predominantly white blood cells in a suspension, including selected white cells (e.g., CD4 and CD8 positive cells) that have been tagged or otherwise labeled, e.g., via a monoclonal antibody, with a fluorochrome. Precisely metered volumes of each of the prepared samples, as provided by a metering mechanism 16, are then sequentially passed through a single, multi-parametric transducer 18 which operates, as described in detail below, to simultaneously measure four different characteristics of each cell in each aliquot, namely, each cell's DC volume (V), its RF conductivity (C), its light scattering properties (S), and its fluorescence (F), as provided by the aforementioned fluorescent stain, or by the fluorochrome tag or label. While the DC volume and RF conductivity each provide a single measurement parameter, the light scattering characteristic of each cell is measured within several different discrete angular ranges, each providing a different measurement parameter.

In the preferred embodiment, light scatter is measured within four different angular ranges, i.e., (a) between about 10 degrees and about 70 degrees, referred to as medium angle light scatters or MALS; (b) between about 10 degrees and about 20 degrees, referred to as lower medium angle light scatter or LMALS; (c) between about 20 degrees and about 70 degrees, referred to as upper medium angle light scatter or UMALS; and (d) between about 80 degrees and about 100 degrees, nominally orthogonal, referred to as side-scatter or SS. Similarly, the fluorescence of a cell is preferably measured within discrete, multiple wavelength ranges, F1, F2, and F3, such ranges being determined by the respective fluorescence emission spectra of the dyes and fluorochromes used to label the cells of interest. Thus, in the embodiment described below, nine different measurements are made on each cell or platelet simultaneously, namely, V and C, plus four light scatter and three fluorescence measurements. Obviously, the number of light scatter measurements can be increased to as many as desired, and the number of fluorescence measurements can be increased (within reason) by increasing the number of photodetectors to correspond to the number of fluorescence spectra emitted by the dye(s) and fluorochrome(s) used to label cells of interest. A discussion of the V, C and S parameters, as well as various other parameters referred to herein, for example, rotated light scatter (RLS) and opacity (RF/DC or C/V), can be found in the commonly assigned U.S. Pat. No. 5,125,737 issued to C. Rodriguez and W. Coulter, the subject matter of which is hereby incorporated herein by reference. The respective transducer outputs, V, C, S and F, are fed to an analyzer 20 which, based on programmed algorithms, operates to differentiate and enumerate the different cell types and subsets in the sample, as well as to determine various blood and cell parameters, e.g., Hgb, Hct, MCV, etc., and to provide a report R. Because the multi-parametric transducer 18 measures all four cell parameters simultaneously, and because precisely metered volumes of sample are passed through the transducer, there is no need to correlate the respective outputs of multiple transducers, as is required by all conventional cell analysis systems, and the accuracy of the analyzer is thus further enhanced. Also, by measuring all four parameters simultaneously on a single cell, a four-parameter multidimensional analysis of each cell is made possible, thereby enabling a more accurate (unambiguous) determination of cell type to be made.

The central component of the cell analyzer briefly described above is the single, multi-parametric transducer 18. As better shown in the enlarged views of FIGS. 2–7, transducer 18 is a specially configured cytometric flow cell FC generally comprising an optical element 30 having an internal passageway 32 through which cells can be made to pass, one-at-a-time (seriatim), for analysis. The center of passageway 32 is located at the geometric center of optical element 30 which narrows to define a cell-interrogation zone Z in which the V, C, S and F parameters of each passing cell are simultaneously determined. Cone-shaped caps 34, 35 are coupled to the opposing end walls 36 of the optical element and serve as a means through which both a blood sample to be analyzed and a sheath liquid, used to hydrodynamically focus or center the sample in the cell-interrogation zone, can be introduced to the optical element and, following passage therethrough, drained to waste. The enclosed chambers 34A, 35A respectively defined by caps 34,35 contain spaced electrodes 38,40 which are connectable to a DC/RF circuit 41 (described below). The components of such circuit operate to (a) produce DC and RF currents through the cell-interrogation zone while cells are passing therethrough, one-at-a-time, and (b) to detect modulations in the respective DC and RF currents, as produced by the passage of cells through the interrogation zone. It is understood that the electrical resistivity of the cells differs from that of the suspending fluid in the sample and sheath fluid, whereby the current modulations are produced. As each cell passes through the interrogation zone, it is irradiated with a focused laser beam B, as provided by a suitable continuous-wave laser 42, and radiation (light) scattered from each cell is detected by a pair of light scatter detectors LSD1 and LSD2. At the same time, fluorescent radiation, if any, emitted by a cell's fluorescent stain or fluorescent label as a result of being excited by the laser radiation, is detected by a florescence-detector FD, described below.

Figure 3:
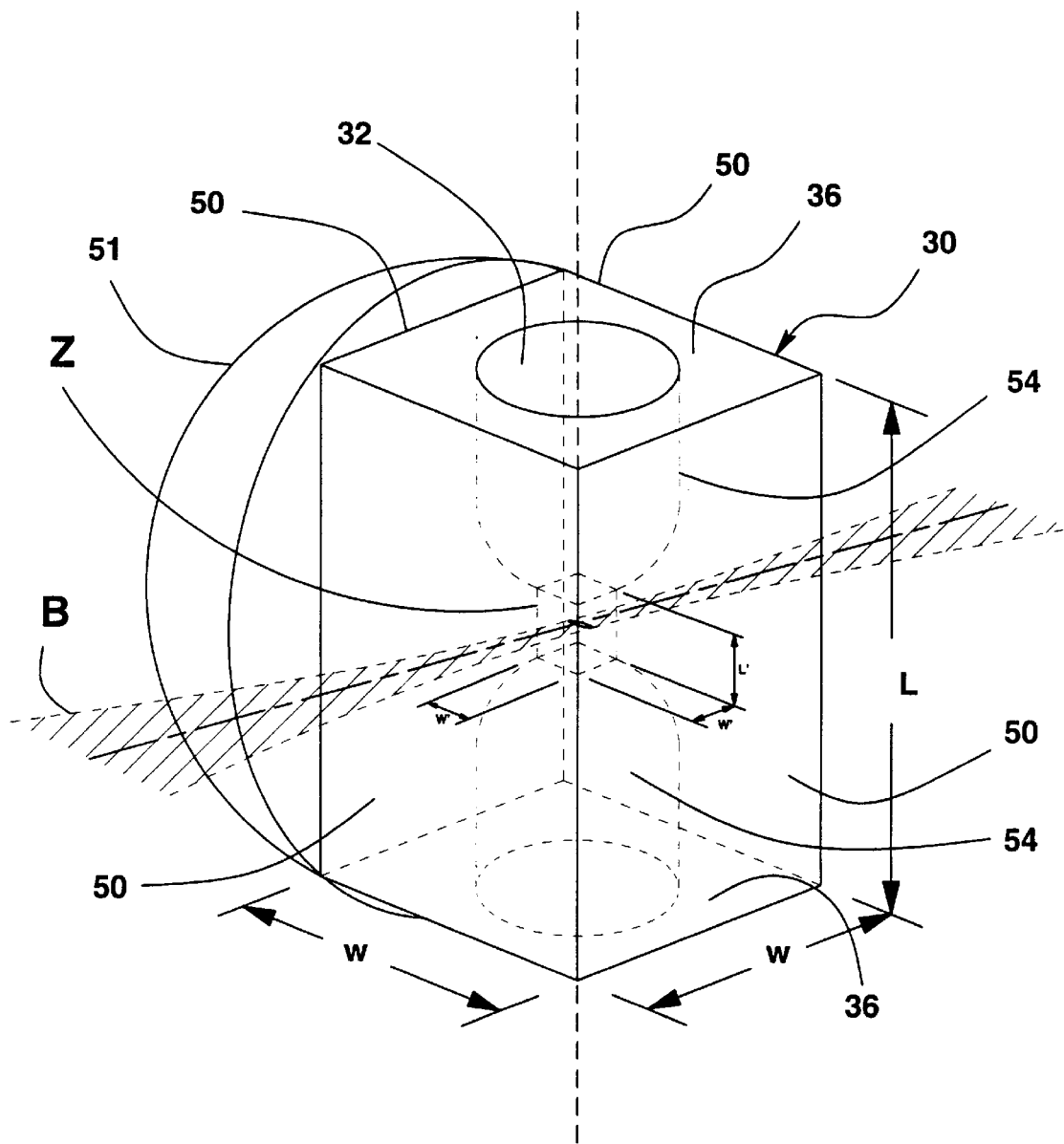
FIG. 3 is an enlarged perspective view of the optical element comprising the multiparametric transducer shown in FIG. 2.

Referring to the enlarged view of FIG. 3, optical element 30 has a square prism shape, comprising four rectangular, optically flat sides 50 and the aforementioned opposing end walls 36. Preferably, the respective widths W of each side 50 are the same, each preferably measuring about 4.2 mm., and the respective length L of each side 50 is about 6.3 mm. It is highly preferred that optical element 30 be fabricated from fused silica, or quartz. The flow passageway 32 formed through the central region of optical element 30 is concentrically configured with respect to the longitudinal axis A passing through the center of element 30 and parallel to the direction of sample-flow. Flow passageway 32 comprises the aforementioned cell-interrogation zone Z and a pair of opposing tapered bore holes 54 having openings in the vicinity of their respective bases that fluidically communicate with the cell interrogation zone. Preferably, the transverse cross-section of the cell-interrogation zone is square in shape, the width W' of each side nominally measuring 50 microns, ±10 microns. It is highly preferred that the length L' of the interrogation zone, measured along axis A, is about 1.2 to 1.4 times the width W' of the interrogation zone, i.e., preferably being about 65 microns, ±10 microns. This geometry has been found necessary to optimize the DC and RF measurements (described below) made on cells passing through the interrogation zone. The maximum diameter of the tapered bore holes 54, measured at end walls 36, is about 1.2 mm. A plano-convex lens 51 is suitably attached (e.g., by optical cement) to one of the flat sides 50 of the optical element, such lens functioning to optically couple fluorescent radiation out of the interrogation zone and onto the fluorescence-detecting photodetector package FD, as discussed below. An optical structure of the type described has been made from a quartz square rod containing a 50×50 micron capillary opening, and subsequently machined to define the communicating bore holes 54.

Figure 2:
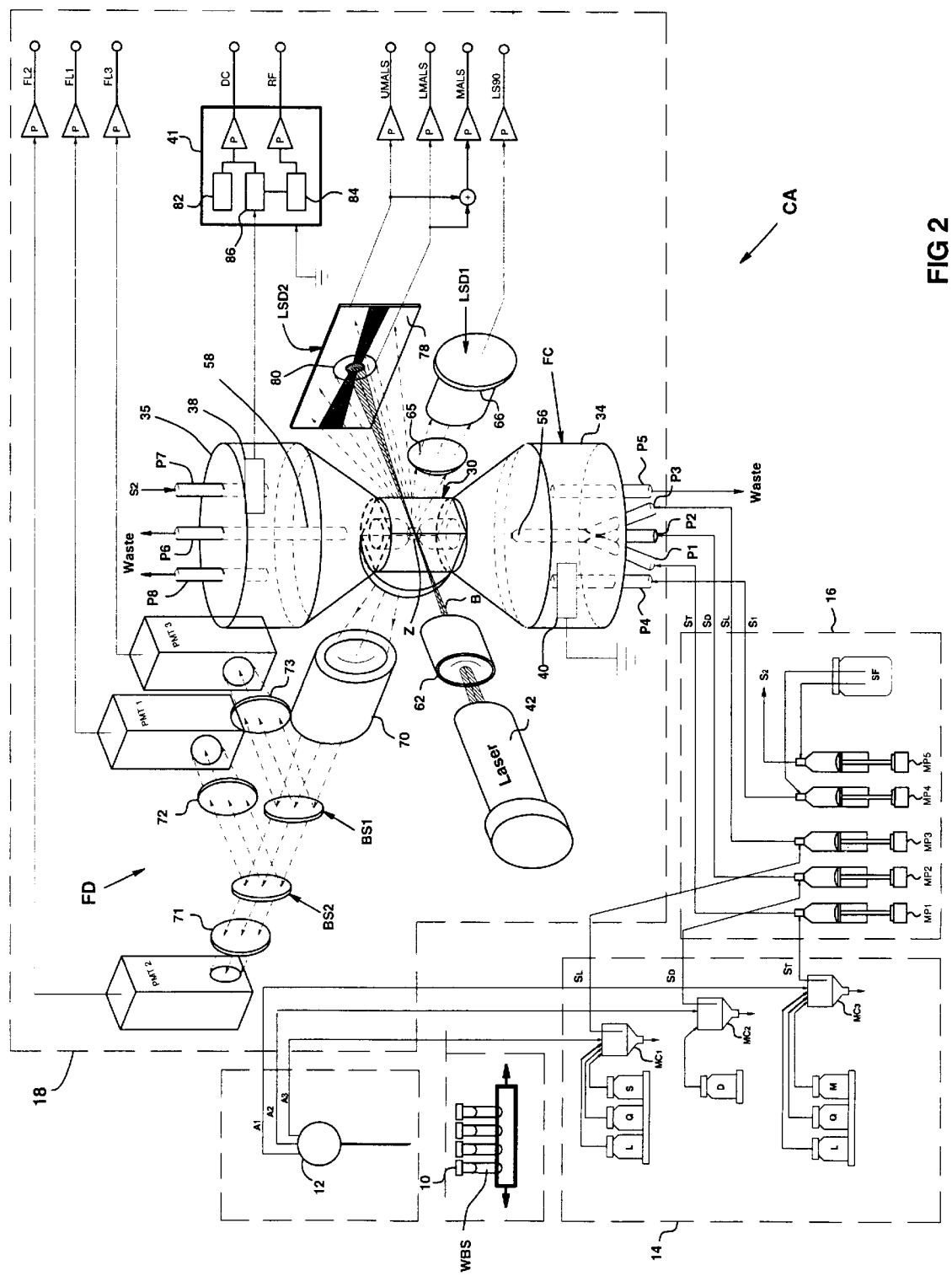
FIG. 2 is a perspective illustration showing many of the components of the FIG. 1 instrument.
Figure 4A:
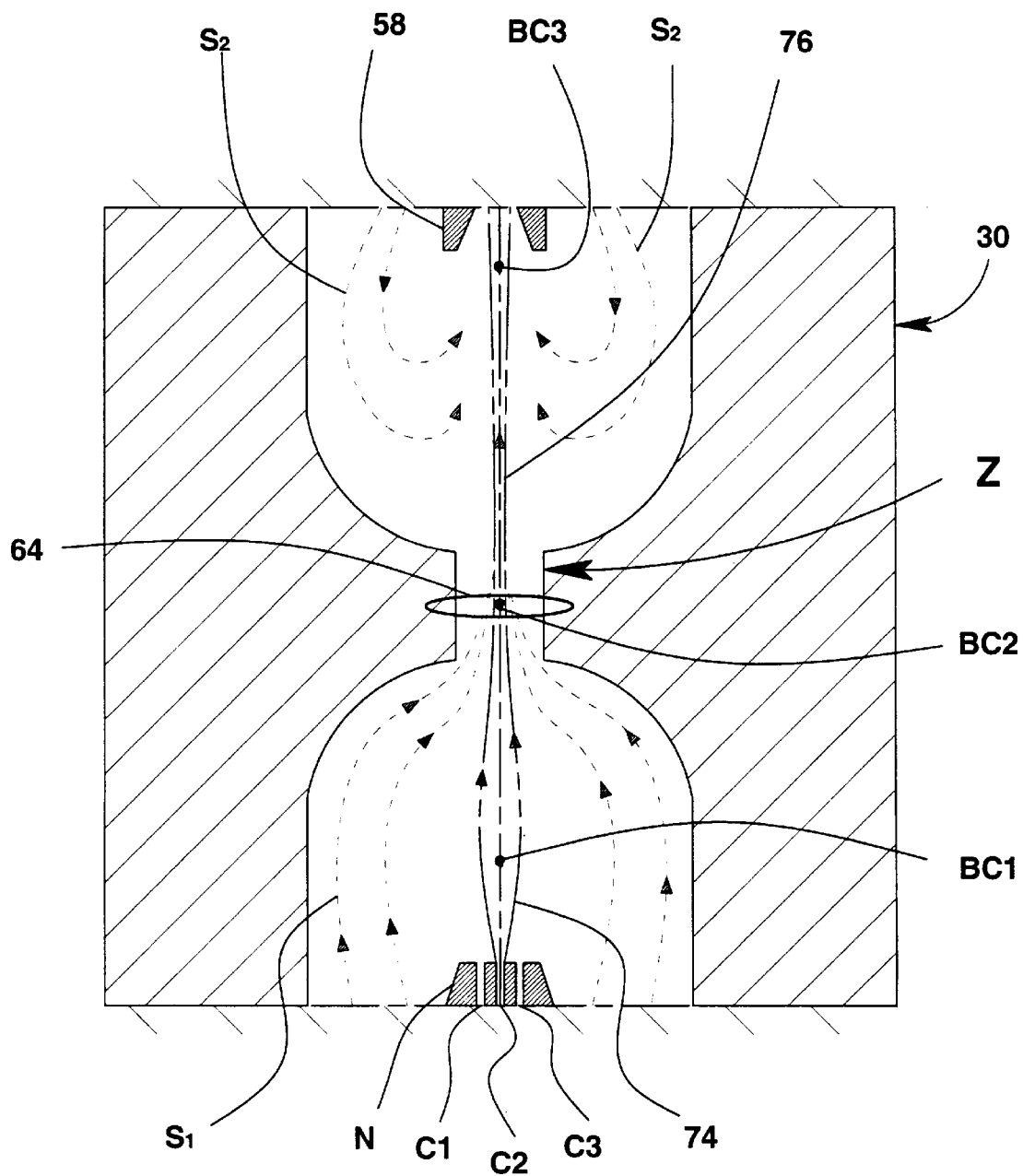
FIG. 4A is a schematic illustration of the transducer of FIG. 3 showing the hydrodynamic flow therethrough.
Figure 4B:
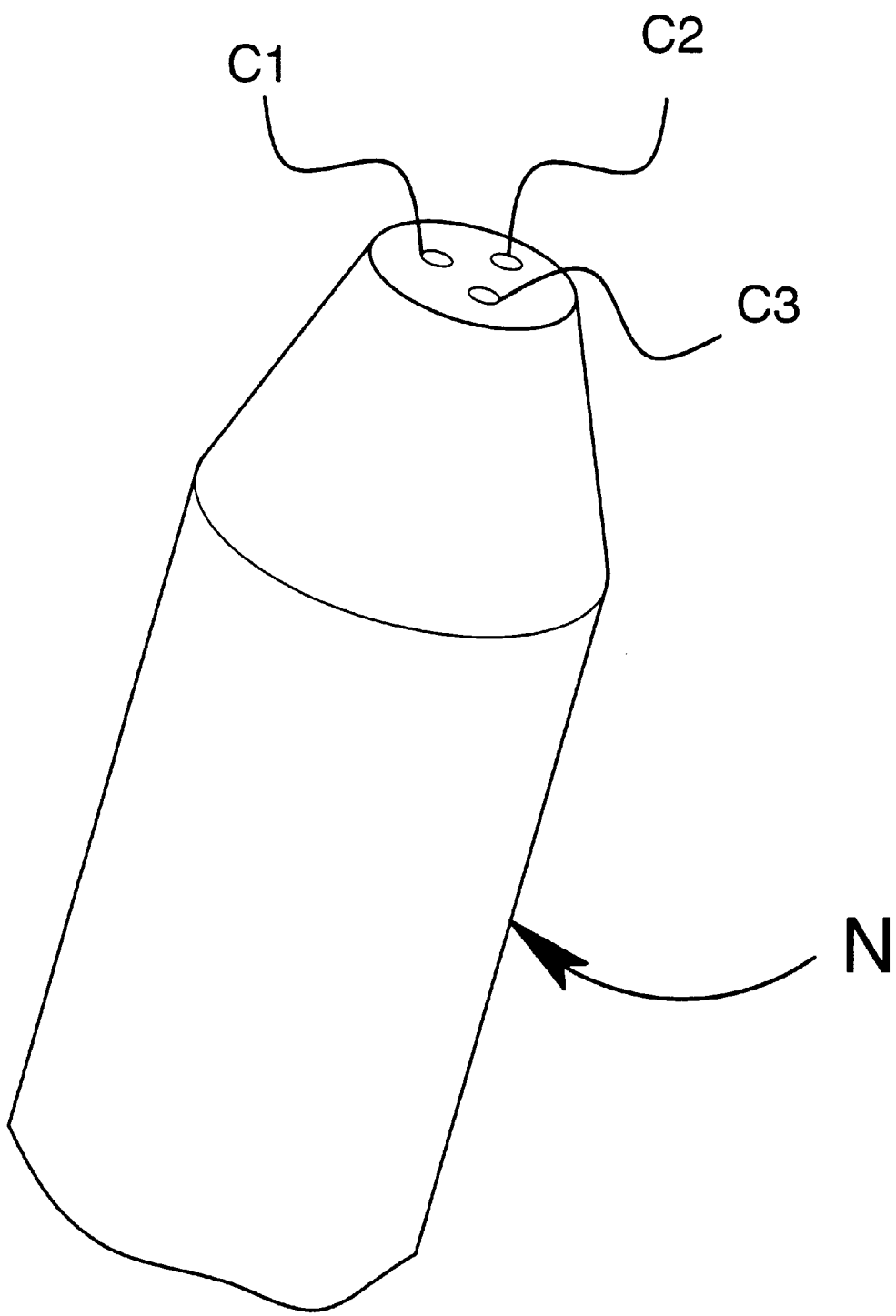
FIG. 4B is a perspective view of a portion of the sample nozzle shown in FIG. 4A.

Referring to FIG. 2, the flow cell's end caps 34, 35 are provided with a plurality of ports P1–P8 which serve to 1) introduce one or more samples to be analyzed and a sheath fluid to the flow cell, 2) drain sample(s) and sheath fluid to waste, 3) flush one or both cap chambers to waste, and 4) provide a vacuum to prime the flow cell lines. Ports P1–P3 are fluidly coupled to the metering mechanism 16 and serve to introduce the metered aliquots $S_L$, $S_D$ and $S_T$ of sample to a multi-channel nozzle N (best shown in FIG. 4B) used to inject the aliquots into passageway 32 for analysis. Port P4 is also coupled to the metering mechanism 16 and serves to introduce metered volumes of a sheath fluid SF to cap 34, such fluid serving to the hydrodynamically focus or center the sample in the cell-interrogation zone. Referring to FIG. 4B, the sample nozzle N, which is partially shown, has three parallel channels, C1, C2, C3, one for each sample aliquot and corresponding to one of the sample-delivering ports P1–P3. As shown in the FIG. 4A example, the metering device 16 of FIG. 2 has delivered a precisely metered volume of sample into the center channel of the sample nozzle N. The latter serves to project the sample towards the interrogation zone Z. Meanwhile, a metered volume of sheath fluid SF that has entered chamber 34A, under pressure and through port P4, flows through passageway 32. In doing so, the sheath fluid uniformly surrounds the sample stream and causes the sample to flow through the center of the cell-interrogation zone Z, thus achieving hydrodynamic focusing. Excess sheath fluid is drained from chamber 34A through port P5. Upon exiting the zone Z, the sample and sheath fluid are collected by a sample exit tube 58, thus preventing re-circulating cells from affecting the DC and RF measurements. In FIG. 4A, a blood cell BC1 is shown exiting the center port of the sample introduction nozzle N, a blood cell BC2 is shown in the center of zone Z and in an elliptically focussed laser beam B (described below), and a blood cell BC3 is shown entering the sample exit tube 58, which is connected to waste. To control the fluid pressure in chamber 35A and thereby control the flow of sample after it exits from the interrogation zone, chamber 35A is maintained full of sheath fluid, such fluid entering through port P7 and draining to waste through port P8.

Figure 5:
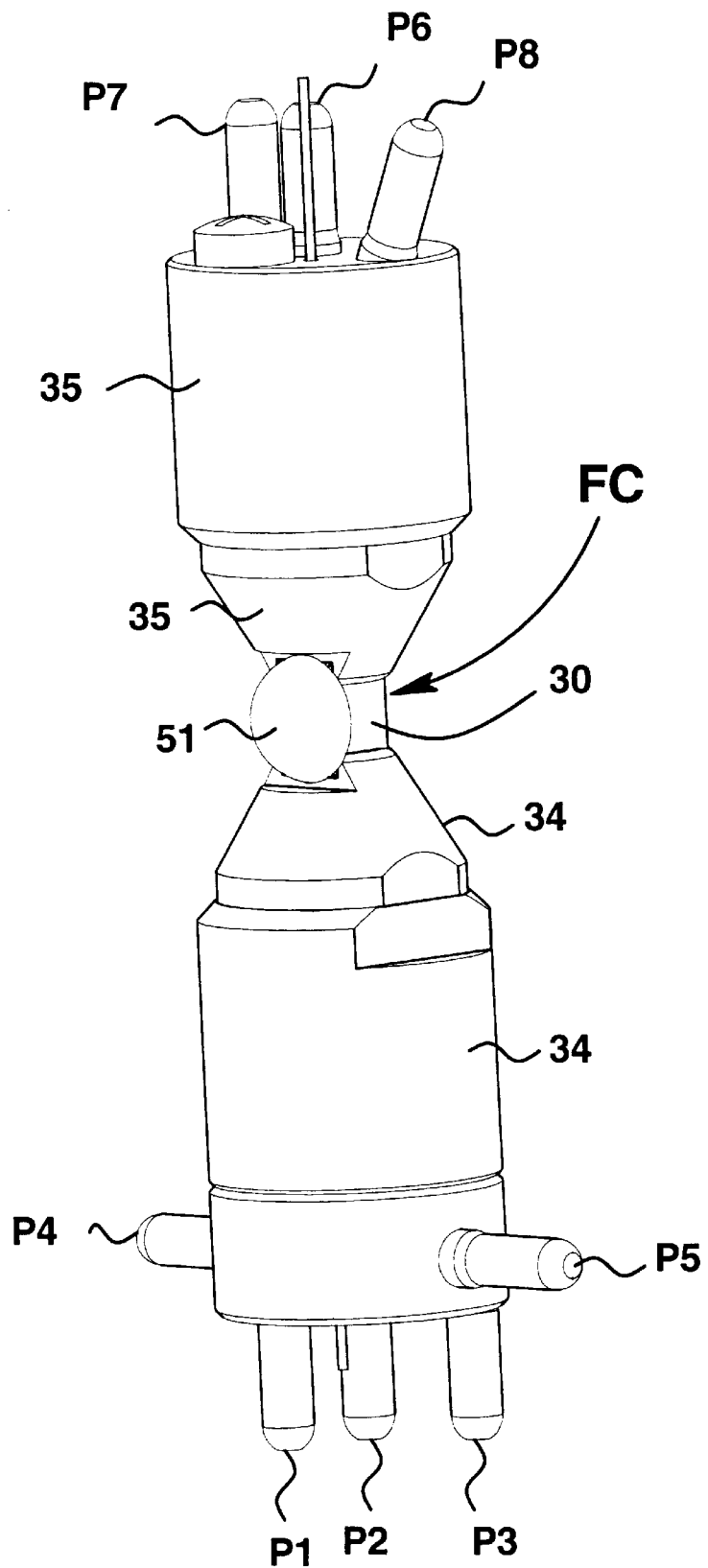
FIGS. 5 and 6 are perspective and cross-sectional views, respectively, of a preferred flow cell used in the FIG. 1 instrument.
Figure 6:
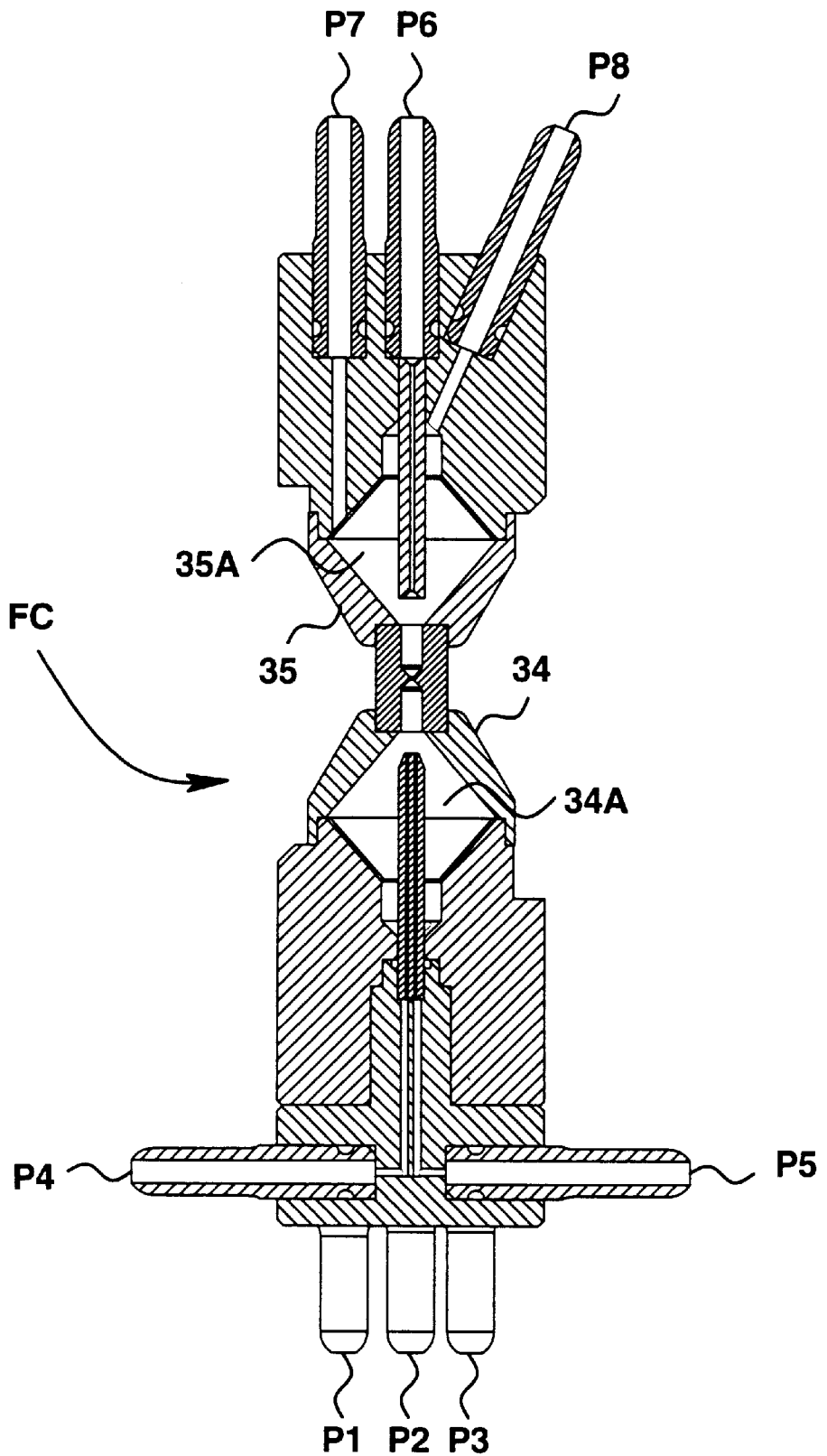
Figure 7:
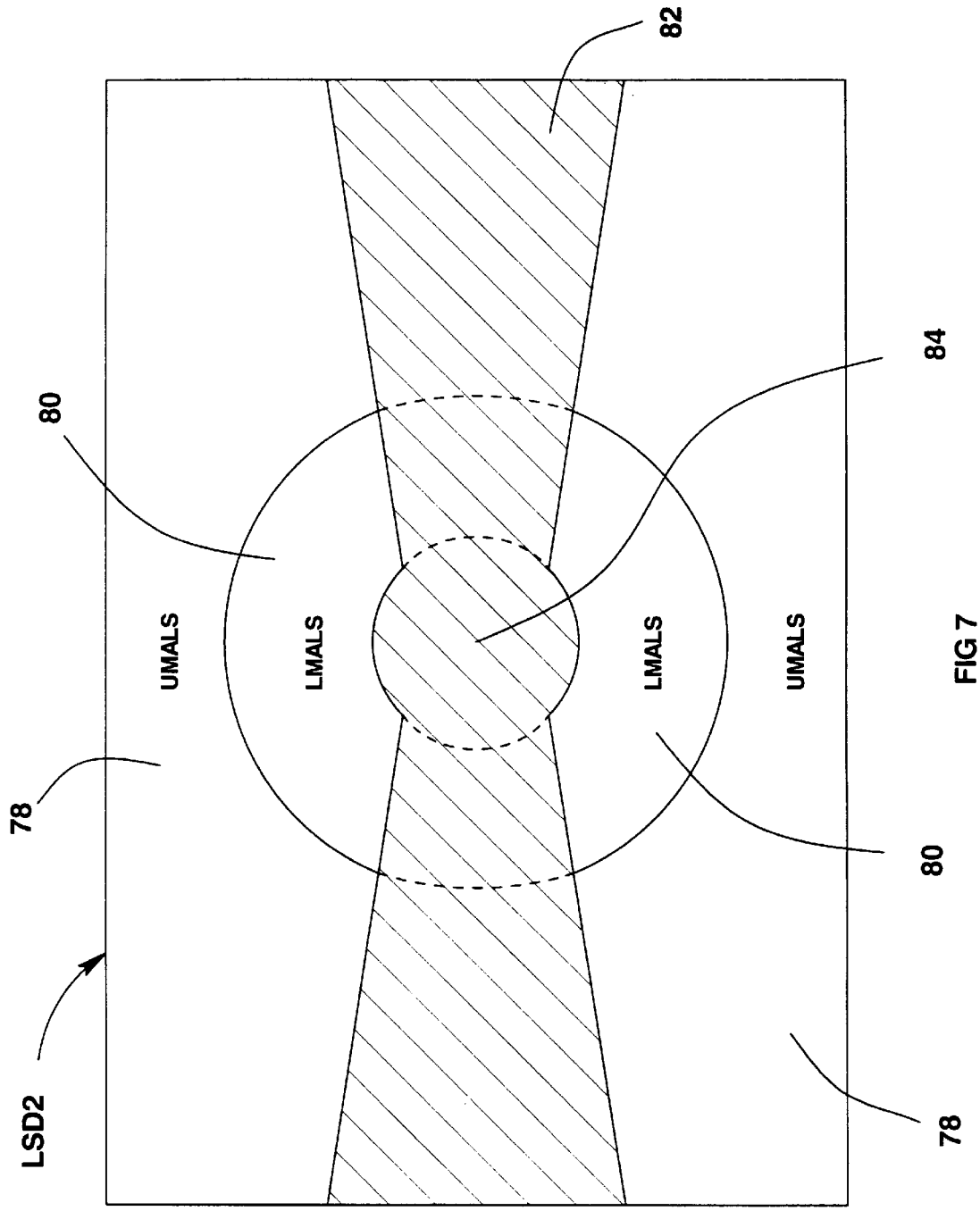
FIG. 7 is a top plan view of discrete elements of the forward light scatter detector forming part of the FIG. 1 instrument.

In addition to the above-described flow cell, the multi-parametric transducer 18 comprises a laser 42 or the like for producing a beam B of radiation having a wavelength adapted to excite a fluorescent material carried by selected cells of interest, and a lens 62 for focusing the laser beam into an elliptically shaped waist 64, shown in FIGS. 3–5. located within the interrogation zone Z at a location through which the cells are caused to pass. Suitable laser sources are a continuous-wave argon laser, which emits at 488 nm., and a diode-pumped solid-state laser emitting at 532 nm. Preferred $1/e^2$ dimensions of the elliptical waist 64 are about 10×100 microns, with the smaller dimension being in the direction of sample flow, i.e., along axis A. Radiation scattered by an irradiated cell, within the interrogation zone is detected by the two light scatter detector units LSD1 and LSD2. LSD1 is located to detect light scattered in a direction substantially normal (i.e., at about 90°±about 10 degree) with respect to the axis of beam B, and LSD2 is located and structured to detect light scattered in a forward plane within an angular range of between about 20 degrees and 70 degrees (MALS). LSD1 preferably comprises a focusing lens 65 which operates to focus side-scattered light onto a pin diode 66 or the like. The latter collects the side scattered radiation and outputs a LS90 pulse signal through a preamplifier P and to the analyzer 20 of FIG. 1. The MALS light scatter detector LSD2, detail shown in FIG. 7, has two photoactive regions, an upper median angle light scatter (UMALS) region 78, and a lower median angle light scatter (LMALS) region 80. As noted above, the UMALS region is adapted to detect light scattered in the angular range of between 20 and 70 degrees, and the LMALS region is adapted to detect light scattered within the angular range of between 10 and 20 degrees. A bow-tie-shaped mask 82 prevents unscattered laser light, as well as light scattered at less than 10 degrees, from striking the LMALS region. Mask 82 also prevents any scattered or diffracted light in the vicinity of the horizontal plane from striking either the UMALS or the LMALS regions. LSD2 produces individual, MALS, UMALS and LMALS pulse signals which are output to the analyzer 20 through suitable preamplifiers P.

Fluorescent radiation emitted by irradiated cells in the interrogation zone is collected by the aforementioned lens 51 affixed to the optical element 30, collimated and spacially filtered by a lens assembly 70 and relayed to a plurality of photomultiplier tubes PMT-1, PMT-2, and PMT-3 through a network of beam-splitting dichroic mirrors, BS-1, BS-2, and filters, 71, 72 and 73. In a conventional manner, each photomultiplier tube detects fluorescent radiation in a wavelength range determined by the optical coatings on the dichroic mirrors and filters. The respective outputs of the photomultiplier tubes are suitably amplified and fed to the analyzer 20 of FIG. 1 as pulse signals FL1, FL2 and FL3.

The DC/RF circuit 41 comprises a DC current source 82, a RF oscillator/detector 84, a coupling circuit 86 and preamplifiers P. The coupling circuit linearly combines the currents produced by the DC source and the RF oscillator/detector, and applies that current to the cell-interrogation zone, as previously described. Preferably, the RF component has a frequency of about 22.5 MHz. As a cell passes through zone Z, the impedance of the zone is altered, resulting in a modulation of the DC current as a function of the cell's physical volume V (often referred to as the DC volume) and a modulation of the RF current as a function of the cell's internal conductivity C. The coupling circuit separates the modulated currents such that a DC pulse signal is conveyed to a DC preamplifier P, and the modulated RF current is detected by the oscillator/detector, resulting in a RF pulse signal which is conveyed to the RF preamplifier P. Both DC and RF pulse signals are output to the analyzer 20.

Referring to FIG. 2, the sample preparation station 14 functions, as noted above, to prepare a plurality of aliquots A1, A2, A3 of whole blood for analysis. Thus, station 14 comprises a plurality of mixing chamber MC1, MC2, MC3, which are adapted to receive aliquots A1, A2, A3, respectively, dispensed from the blood sampling valve 12 by a suitable pump (not shown). As shown, mixing chamber MC1 is positioned to receive a first aliquot A1 of whole blood and to mix it with a diluent D which may contain a fluorescent dye. In this manner, a diluted sample $S_D$ is prepared for red cell/platelet analysis. Similarly, mixing chamber MC2 is positioned to receive a second aliquot A2 of whole blood for analysis. In mixing chamber MC2, the whole blood sample is subjected to a suitable lysing reagent L, a quenching reagent Q and, optionally, a fluorescent stain S. In this manner, the red cells are eliminated from the sample, and the sample is prepared for a white cell differential analysis. In a like manner, a third aliquot A3 is dispensed to mixing chamber MC3 which is positioned to receive a reagents adapted to prepare the sample for extended analysis using monoclonal antibodies to label selected cells with fluorochromes. Such reagents may include a lysing reagent L, a quench Q and fluorochrome tagged monoclonal antibodies M.

As shown in FIG. 2, the metering station 16 comprises a plurality of metering pumps MP1–MP5. Each pump is preferably of the syringe variety, each being driven by a suitable stepping motor (not shown) which operates under the control of controller 11 to pump liquids at a precise rate. Metering pumps MP1–MP3 are dedicated to delivering predetermined volumes of the samples $S_L$, $S_D$ and $S_T$ from their respective mixing chambers MC1–MC3 and to the input ports P1–P3 of the flow cell at fixed rates. In a known manner, metering pumps MP4 and MP5 serve to supply metered volumes of a sheath fluid SF to the flow cell, such fluid serving to hydrodynamic focus of the cells in the sensing zone Z.

While the apparatus of the invention can be operated to analyze each of the samples $S_L$, $S_D$ and $S_T$ alone so as to provide, for example, only a red cell analysis or only a five-part differential of white cells, it is preferred that at least two analyses be performed in tandem so as to assure that the sample has not changed appreciably between analyses. As noted above, however, it is not necessary to correlate the results of one analysis with another, e.g. the red cell analysis with the white cell analysis to obtain useful results. Thus, for example, aliquots A1 and A2 are delivered to their respective chambers MC1 and MC2. The diluted and stained sample $S_D$ is primed and analyzed in the transducer 18 while the lysed and stained sample $S_L$ is still being prepared. The flow cell FC is rinsed to allow the next sample to be analyzed without any contamination. The lysed and stained sample $S_L$ is then primed and analyzed in the transducer 18.

Figure 8:
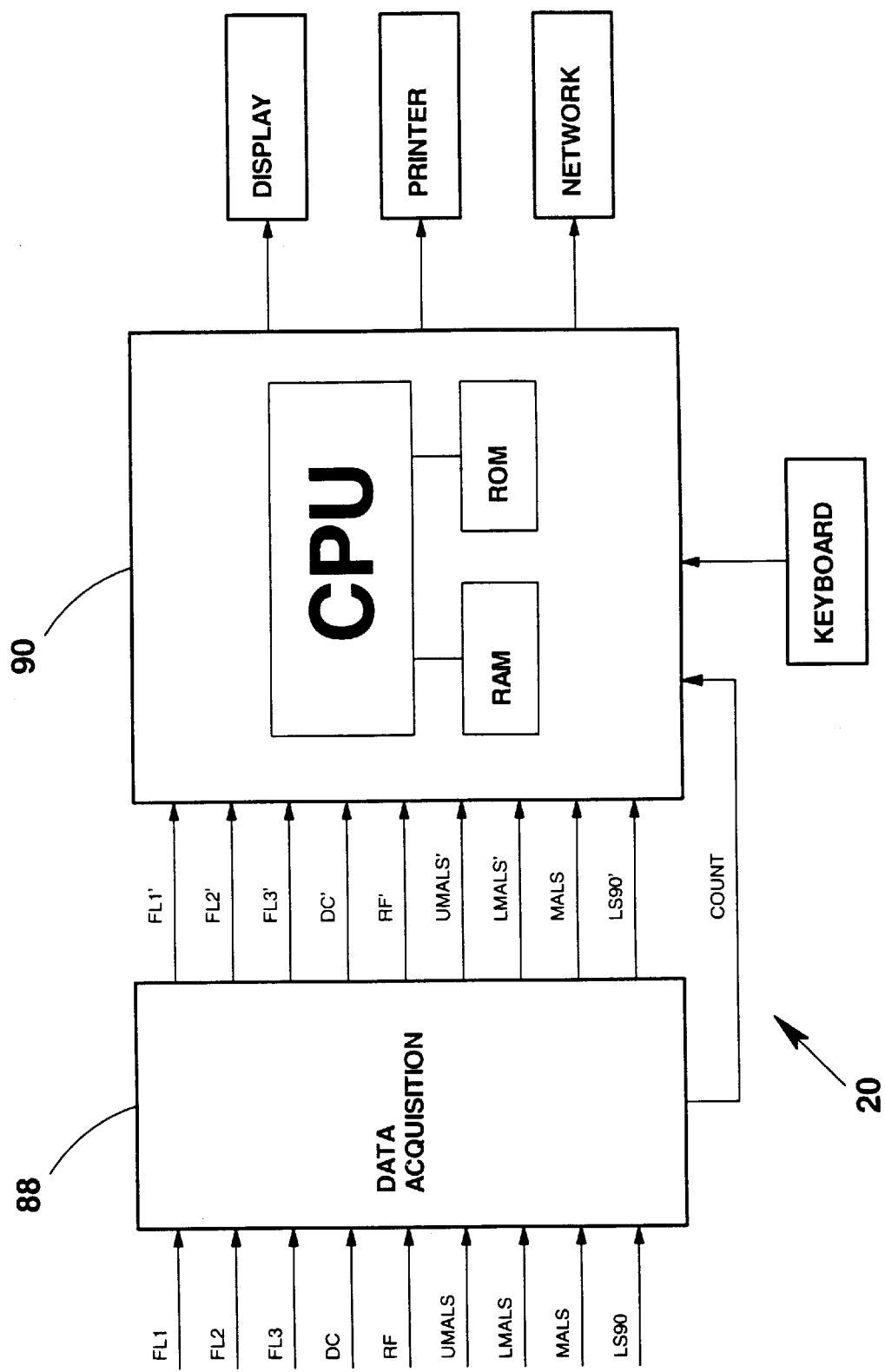
FIG. 8 is a schematic of the elements comprising the data analyzing component of the FIG. 1 instrument.

Referring to FIG. 8, analyzer 20 consists of a data acquisition module 88 and a computer 90. The data acquisition module 88 inputs pulse signals (FL1, FL2, FL3, DC, RF, UMALS, LMALS, LS90) from the VCSF transducer; amplifies, filters and counts the pulse signals; obtains pulse information, e.g., peak voltage, from each of the pulse signals; and converts the pulse information to digital values (FL1', FL2', FL3', DC', RF', UMALS', LMALS', LS90'). The pulse peak digital values and the pulse count(s) are transferred to the computer 90 for classification, enumeration and characterization. The computer 90 includes standard components such as central processing unit (CPU), random access memory (RAM), read-only memory (ROM), keyboard, display, printer, and network connection.

The operation of the blood-analyzing instrument described above will be evident from the ensuing working examples.

EXAMPLE 1

The above-described automated cell analyzer was used to carry out the method described below for differentiating and enumerating red cells and platelets. The method utilizes a diluent D (see FIG. 2) comprising the following components:

1. Phosphate Buffered Saline (PBS)
2. Coriphosphine-O (CPO)-8 µg/ml
3. Dodecyl-β-D-maltose-20 µg/ml
4. Proclin 300–0.05%

CPO is a membrane-permeable, fluorescent dye molecule having a high affinity for nucleic acids. CPO is a metachromatic molecule that, when excited with light at a suitable wavelength, will emit fluorescence at a wavelength determined by the molecular structure of the substance to which it is attached. Thus, when used to stain a cell containing both DNA and RNA (both being nucleic acids), CPO will fluoresce at one wavelength (FL1) when attached to the cell's DNA content and at another wavelength (FL2) when attached to the cell's RNA content. Referring to FIG. 2, about 2 μl of the whole blood aliquot A1 is delivered to a mixing chamber MC1 in the sample prep station and mixed with 2 ml of diluent D for about 2 seconds to produce a diluted sample $S_D$. A portion of sample $S_D$ is drawn by a vacuum (applied to flow cell port 5) from the chamber MC1 and into a line connecting this chamber and port P1 of the flow cell, thereby pre-charging the line with sample. Metering pump MP1 is operated by a stepper motor to advance the sample through the flow cell at a rate of 2 microliters/sec. for a ten second interval. During this time interval, all cells passing through the interrogation zone Z were counted and differentiated (i.e. characterized as to type or subset). Thus, a precise volume of 20 microliters of sample is presented for analysis. At the same time, metering pump MP4 delivers sheath fluid at a rate of about 8 microliters/sec. Owing to the difference in area of the ports P1 and P4 the sample and sheath fluids pass through the flow cell at the same rate. The total incubation time, which includes mixing and priming, is nominally 5.5 seconds, with a working range of 5 to 15 seconds. As described earlier, V, C, S and F measurements are made on every cell in the single multi-parametric transducer 18, and measurement data are processed, in a conventional manner, by the analyzer 20 to yield a report which provides absolute counts of red cells and platelets, absolute and relative concentrations of reticulocytes and reticulated platelets, cellular hemoglobin information for red blood cells and reticulocytes, mean volumes of the aforementioned cell types, and derived parameters, including total hemoglobin, for the sample.

Figure 9A:
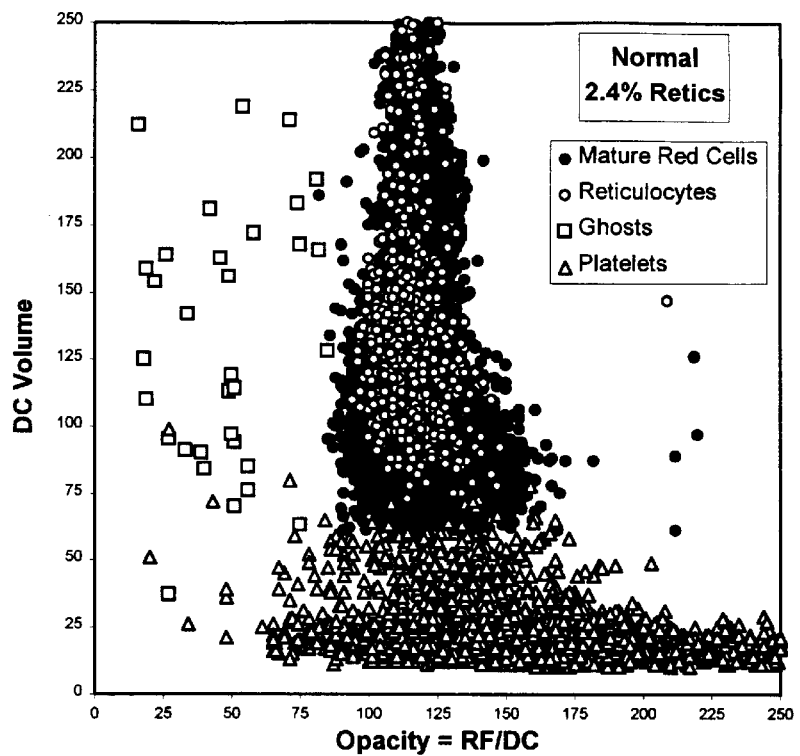
FIGS. 9A–23 are scattergrams illustrating data acquired by the FIG. 1 instrument.
Figure 9B:
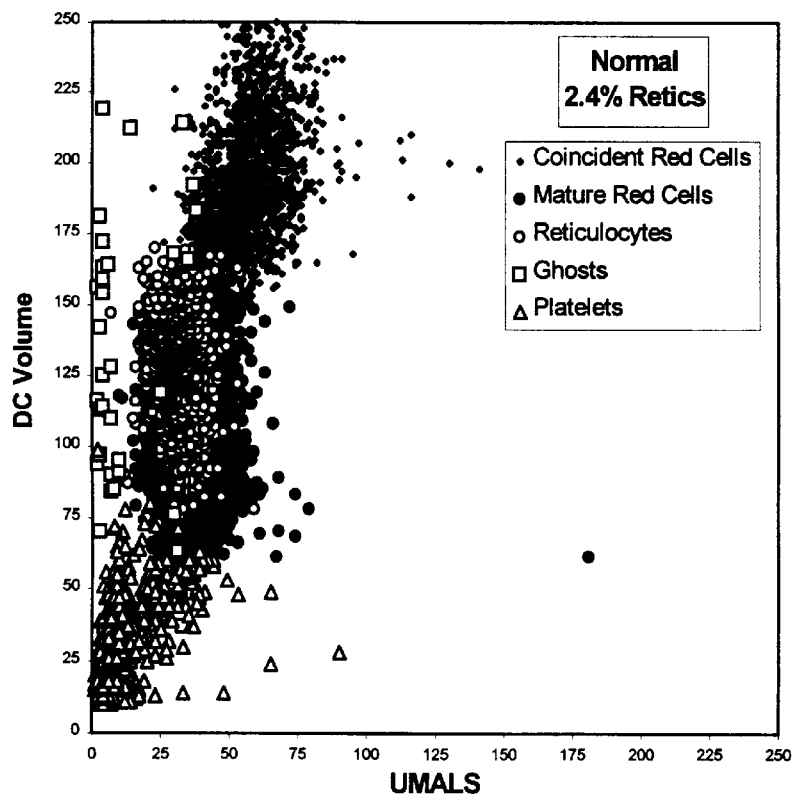
Figure 9C:
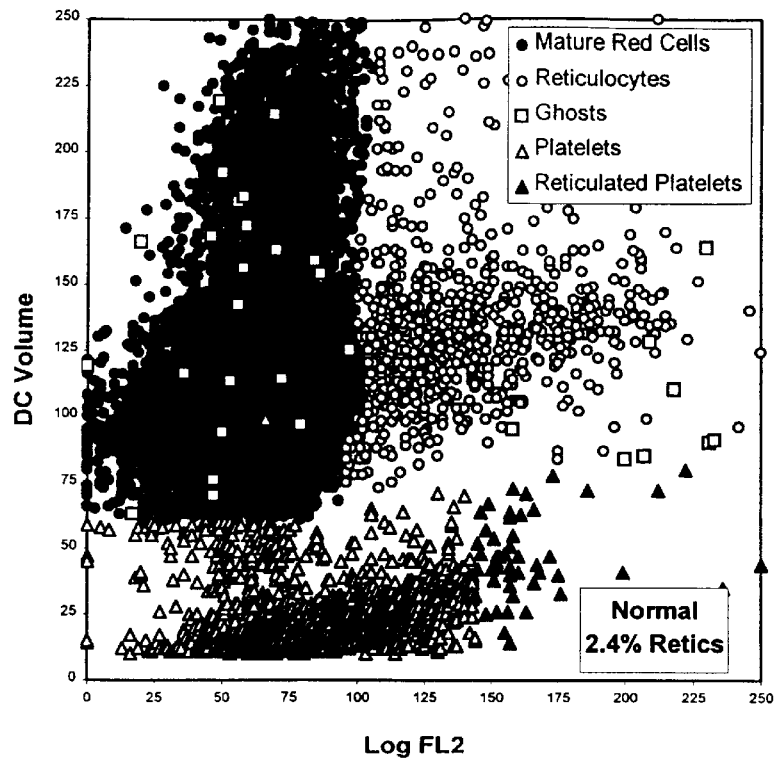

CPO is the preferred nucleic acid fluorescent dye, but other similar dyes can be used to yield acceptable results. The dodecyl-β-D-maltoside component has two functions: 1) It acts as an isovolumetric cell sphering reagent to enable the measurement of erythrocyte cell-by-cell hemoglobin (HC), and 2) promotes a significant increase in dye penetration through the cell membrane and nucleic acid staining, resulting in about a hundred-fold reduction in staining time (which is about 60 minutes in standard flow cytometry). Proclin 300 is an anti-bacterial agent. CPO can be excited with an argon-ion laser at 488 nm or a diode-pumped solid state laser operating at 532 nm, which is the preferred excitation for this example. The fluorescent detection system FD is set up to receive emission at 575 nm (FL1) which responds primarily to dye interaction with DNA, and at 675 nm (FL2), which responds primarily to dye interaction with RNA. In this example, the RNA is the signal (FL2) of interest and is labeled as "Fluorescence" in the subsequent figures. FIG. 9A is a scattergram showing the Volume (DC) plotted against Opacity (RF/DC) for red cells and platelets. Mature red cells and reticulocytes overlap and appear as a single population of red cells. Platelets appear at lower volume. Ghosts (i.e., red cells that have lost their hemoglobin) comprise a very small number of red cells which are damaged and, thus, need to be removed from the HC measurement. FIG. 9B shows DC Volume vs. UMALS. While the patterns are analogous to those of FIG. 9A, an additional cluster of coincident red cells, caused by two or more red cells traversing the aperture simultaneously, is identified. Coincident red cells are also removed from the HC measurement, but are taken into account when measuring reticulocyte percent (RET %) and absolute concentration (RET#). FIG. 9C shows DC Volume vs. Fluorescence of the red cells and platelets. Mature red cells and reticulocytes are easily discerned. Ghost red cells can be mature red cells or reticulocytes and do not affect the results. A cluster of reticulated platelets is discerned to the right (higher fluorescence) of the main platelet population.

Figure 10A:
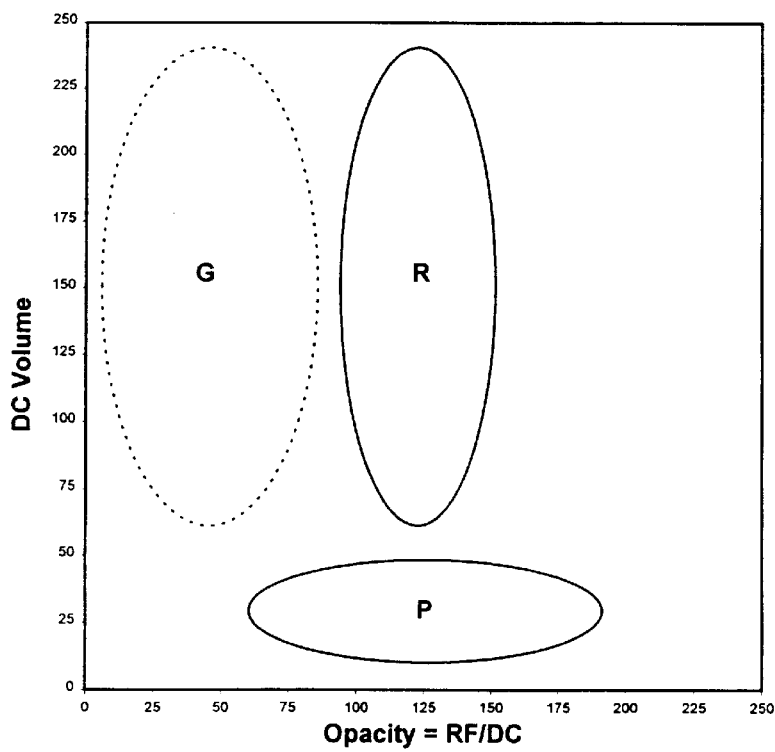
Figure 10B:
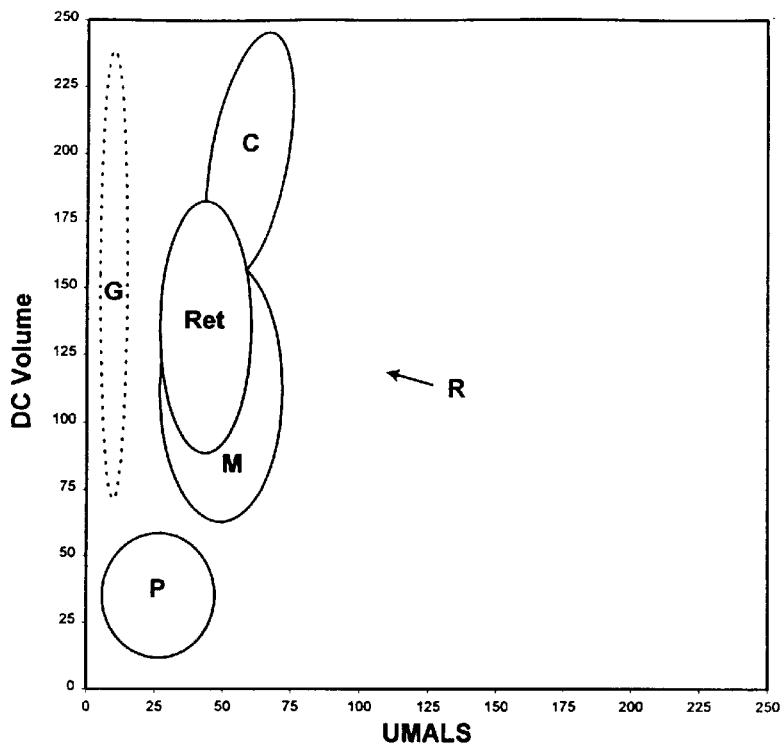
Figure 10C:
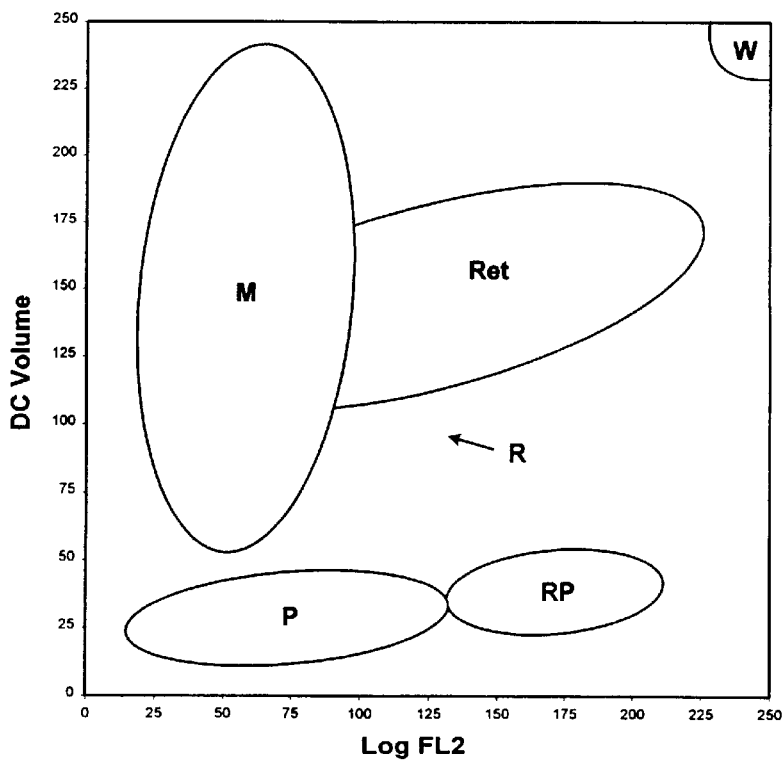

A preferred data analysis method is described as follows: Referring to FIG. 10A, DC Volume and Opacity are used to identify platelets P, red cells R and ghosts G. Referring to FIG. 10B, DC Volume and UMALS are used to refine the identification of platelets P and ghosts G versus red cells R. Identify coincident red cells C vs. non-coincident mature red cells MC plus reticulocytes RET. Referring to FIG. 10C, DC Volume vs. FL2 is used to identify mature red cells MC and reticulocytes RET, both coincident and non-coincident, and identify a reticulated platelets RP subpopulation of platelets P. White cells W are differentiated in this analysis due to their higher DC Volume and significantly higher fluorescence level on FL2 and FL1 (not shown). Using the classification obtained with Volume, Opacity, UMALS and Fluorescence, and using the cell count information obtained from DC Volume or any of the other simultaneous measurements, report reticulocyte percent (RET %), reticulated platelets, or immature platelet fraction percent (IPF %) and absolute concentration (IPF#). Also report absolute concentrations for the following populations: Red cells (RBC), reticulocytes (RET#), platelets (PLT), reticulated platelets, and white cells (WBC). Using the aforementioned parameters, perform a characterization of the red cell subpopulations: Referring to FIG. 10B, and using a function of UMALS and Volume, obtain cell-by-cell hemoglobin for reticulocytes (CHr) and all red cells (CH), both of which can be histogrammed to provide additional clinical information. Also obtain the mean of cell-by-cell hemoglobin for reticulocytes (MCHr) and total red cell mean corpuscular hemoglobin (MCH). Using DC Volume, compute mean platelet volume (MPV), mean reticulocyte volume (MRV), total red cell mean corpuscular volume (MCV), and red cell distribution width (RDW). Compute hematocrit (HCT)=MCV×RBC/10. Compute total hemoglobin (HGB)=MCH×RBC. Compute mean corpuscular hemoglobin concentration (MCHC)=MCH/MCV.

EXAMPLE 2

The above-described automated cell analyzer was used to carry out the method described below for providing an extended white cell differential. The method utilizes a metachromatic dye (CPO 625 ug/ml), a red blood cell lysing reagent and a quenching reagent to retard or further inhibit the effects of the lyse on the remaining unlysed cells. Examples of two different preferred lysing and quenching reagents, their volumes and exposure times are shown in the following table. Alternative lysing and quenching reagents might also be employed with the requirement that the reagents efficiently lyse the RBC's while preserving the desired electro-optical characteristics of the remaining cells (WBC's and NRBC's).

TABLE 1

| Blood Volume | Lyse | Volume & Timing | Quench | Volume & Timing |
|---|---|---|---|---|
| 34 ul | Erythrolyse II (Beckman Coulter, Inc.) | 507 μl/ 5.3 seconds | Stabilyse (Beckman Coulter, Inc.) | 200 μl/ 8.5 seconds |
| 34 ul | Lysing Reagent (Disclosed in U.S. | 556 μl/ 4 seconds | Stabilyse (Beckman | 200 μl/ 8.5 seconds |

TABLE 1-continued

| Blood Volume | Lyse | Volume & Timing | Quench | Volume & Timing |
|---|---|---|---|---|
| | Pat. Appln. No. 08/898,000 filed July 25, 1997) | | Coulter, Inc.) | |

Referring to FIG. 2, 34 μl of aliquot A2 is delivered to a mixing chamber MC2 in the sample prep unit 14 and mixed with 3.4 μl of CPO for 30 seconds. Referring to the above table, 507 μl of Erythrolyse II is then added to the CPO stained blood and mixed for an additional 5.3 seconds at which time 200 μl of Stabilyse is added with continued mixing for an additional 8.5 seconds.

Using metering pump MP2, a volume of the sample $S_L$ is passed through the flow cell for a preset time interval and, using the procedure described in Example 1, all cells in a 40 microliter volume of sample $S_L$ are interrogated. As described earlier, V, C, S and F measurements are obtained from every cell in the sample, and these measurements are processed by the analyzer 20 to yield a report which provides absolute and relative concentrations of the five normal white cell types and at least one abnormal cell type, including, but not limited to, nucleated red blood cells (NRBC), blasts and immature cells. CPO can be excited with an argon-ion laser at 488 nm or a diode-pumped solid state laser operating at 532 nm, which is the preferred excitation for this example. The fluorescent detection system FD is set up to receive emission at 575 nm (FL1), which responds primarily to dye interaction with DNA, and at 675 nm (FL2), which responds primarily to dye interaction with RNA.

Figure 11A:
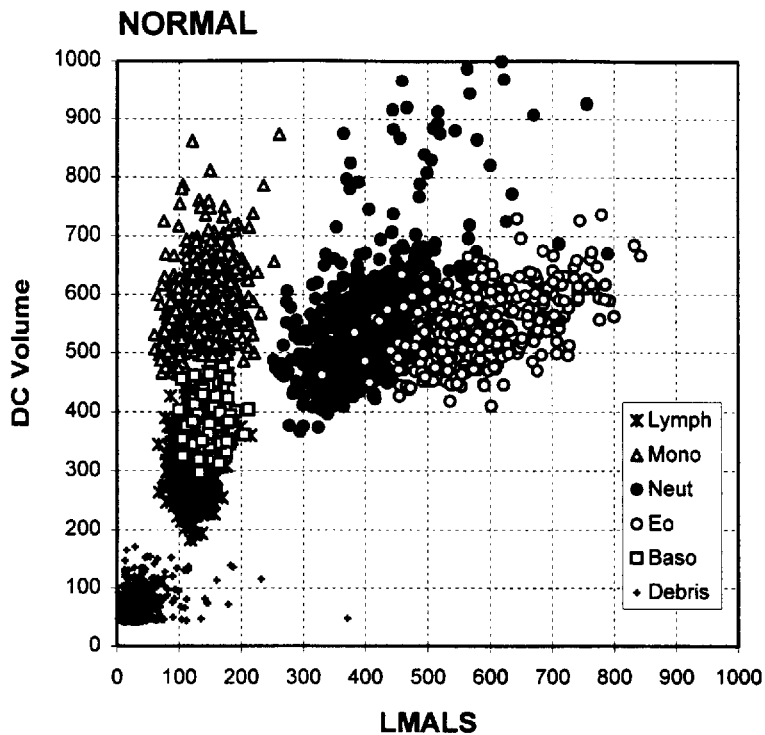
Figure 11B:
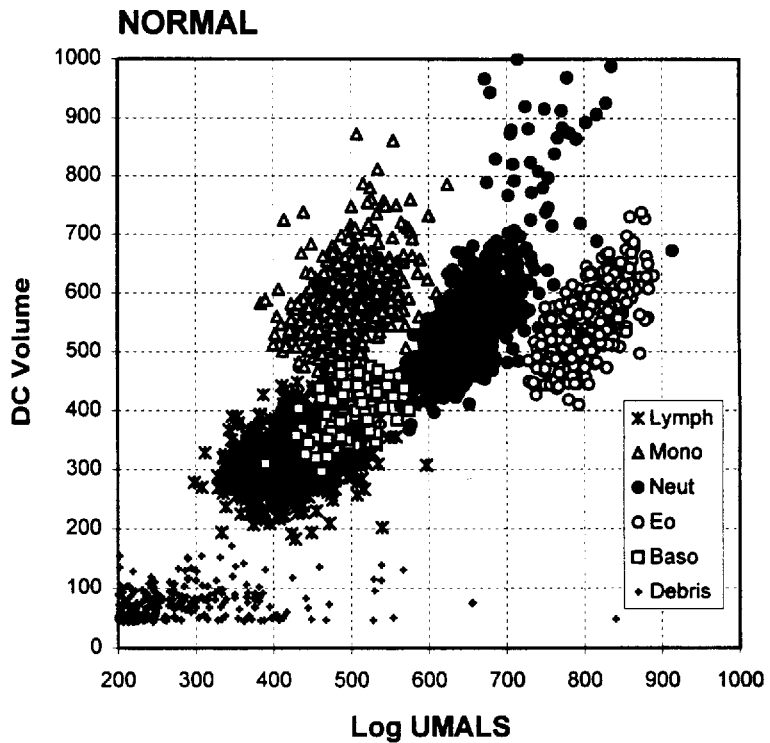
Figure 12A:
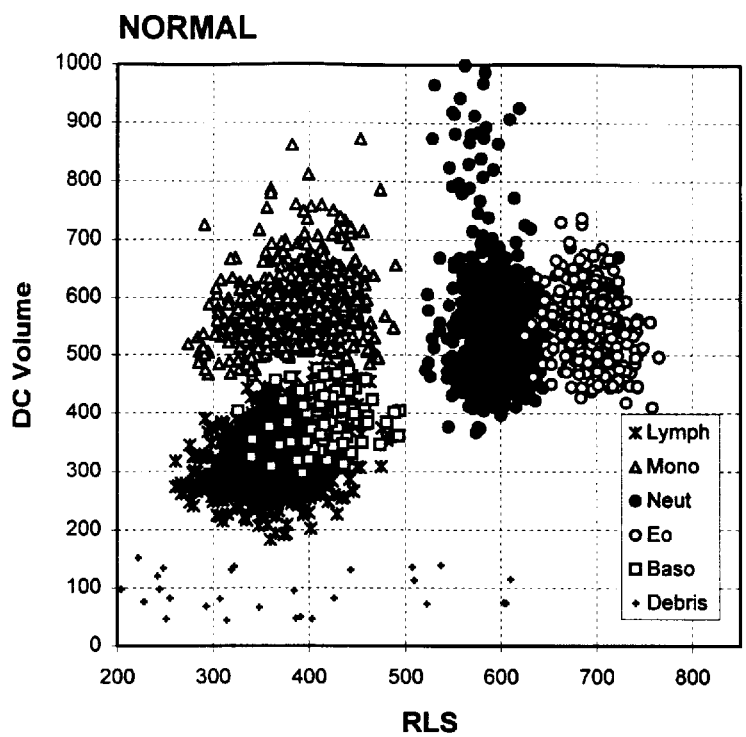
Figure 12B:
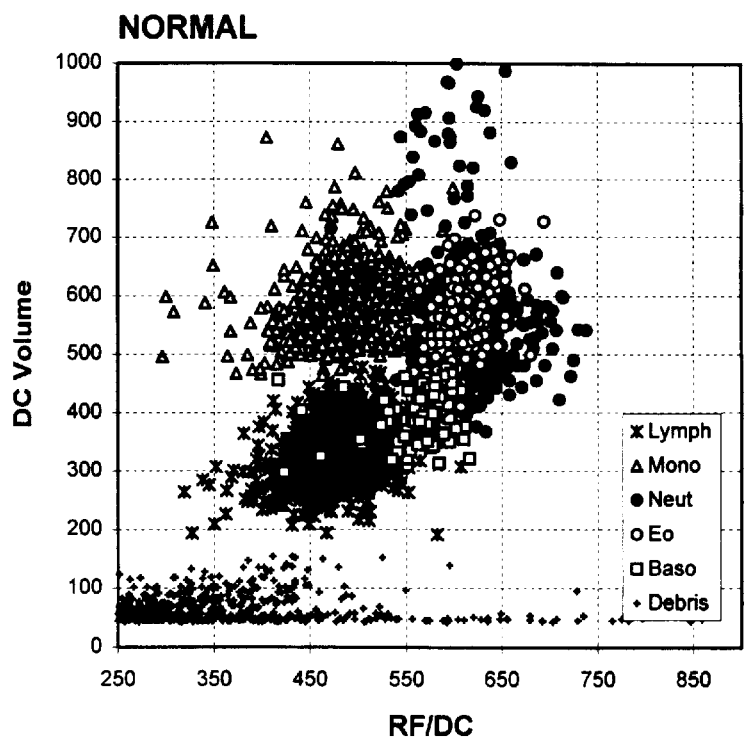
Figure 13A:
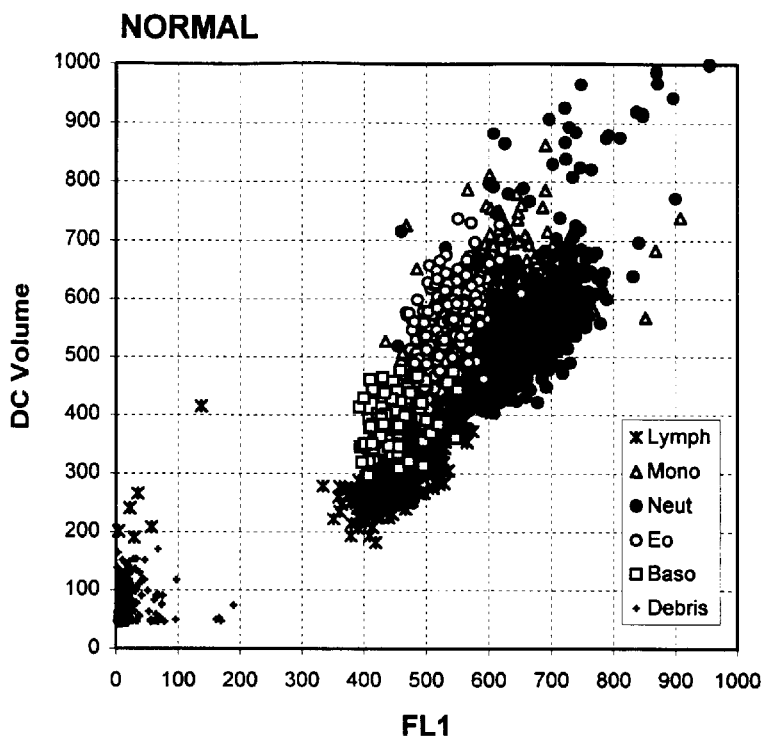
Figure 13B:
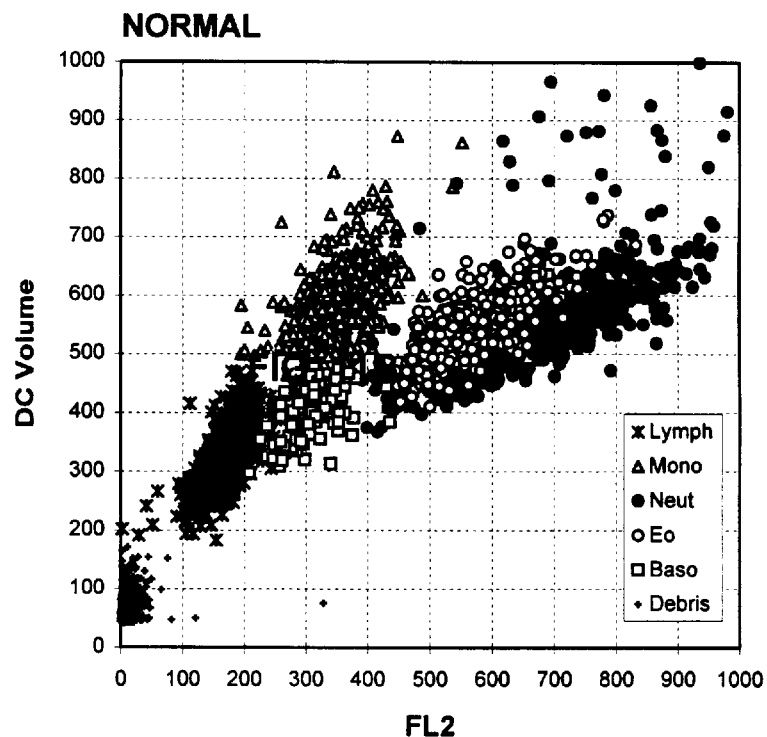
Figure 14A:
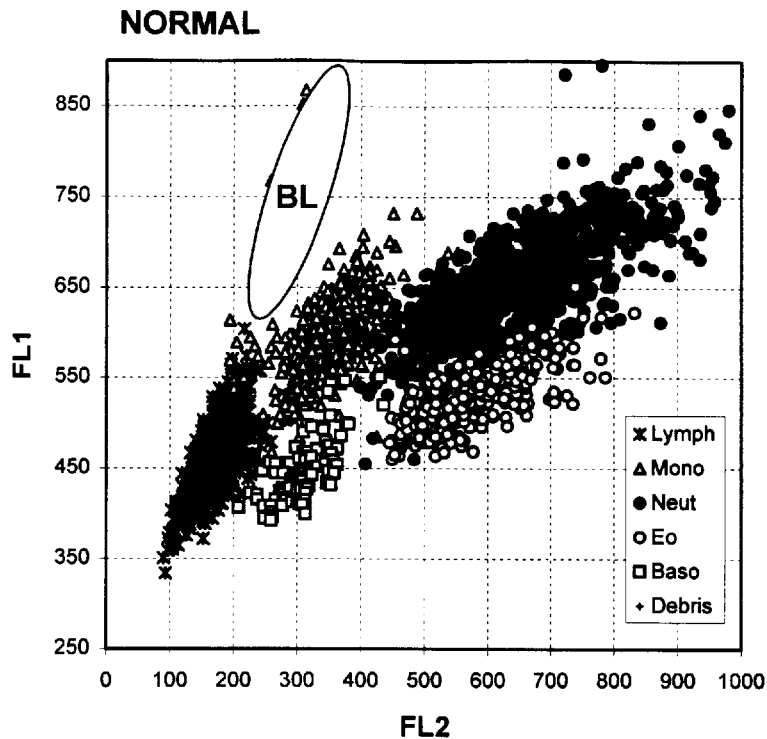
Figure 14B:
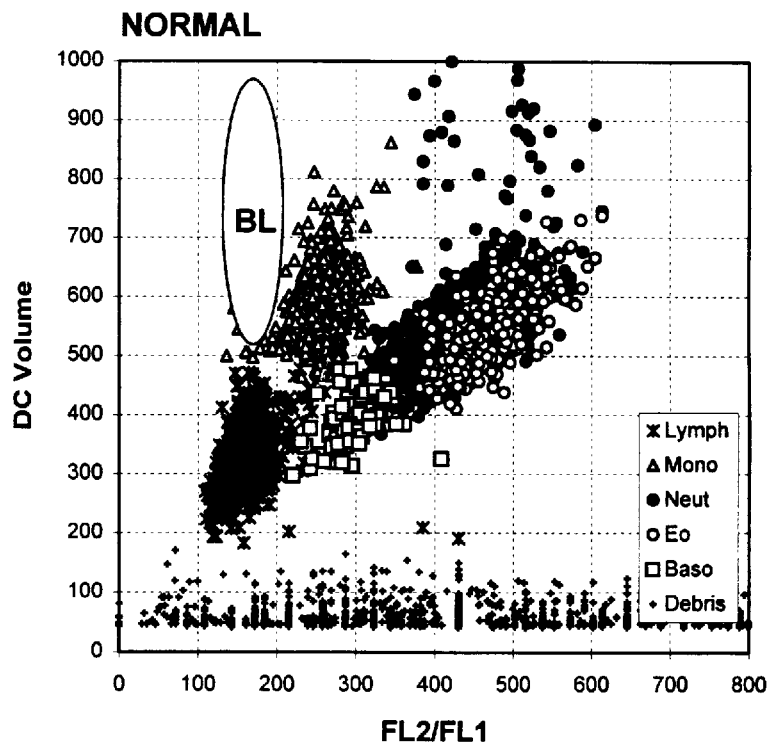
Figure 15A:
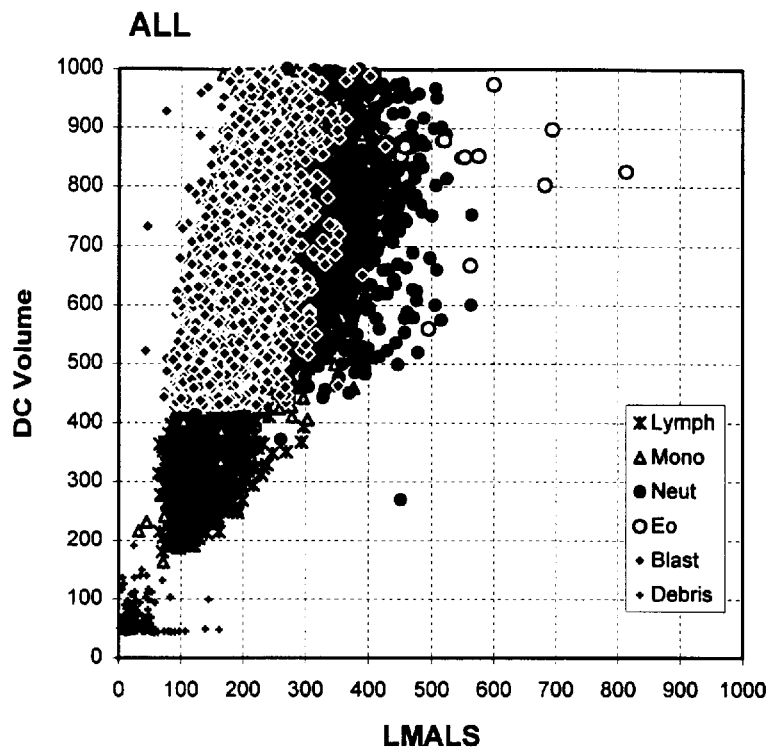
Figure 15B:
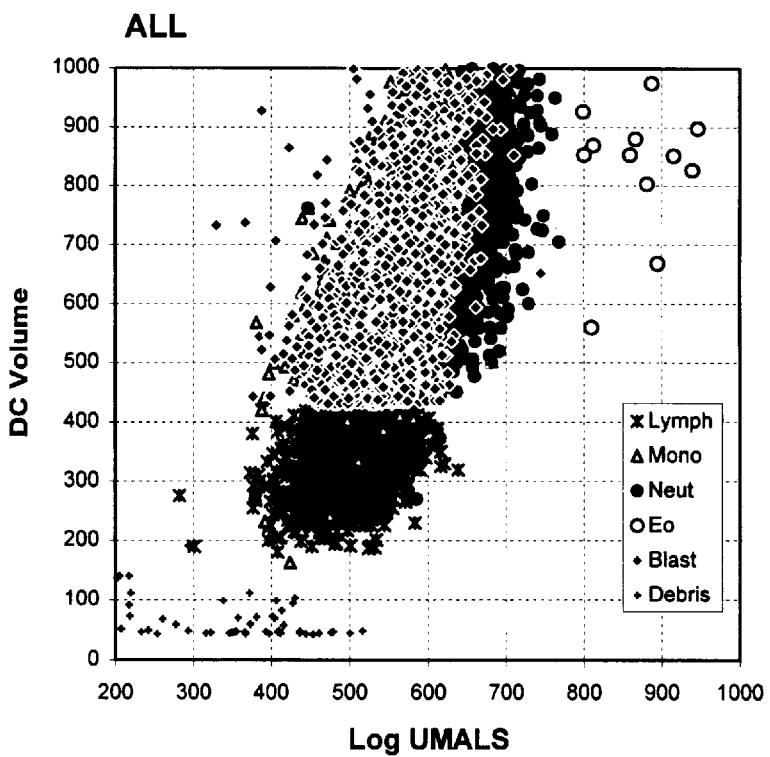
Figure 16A:
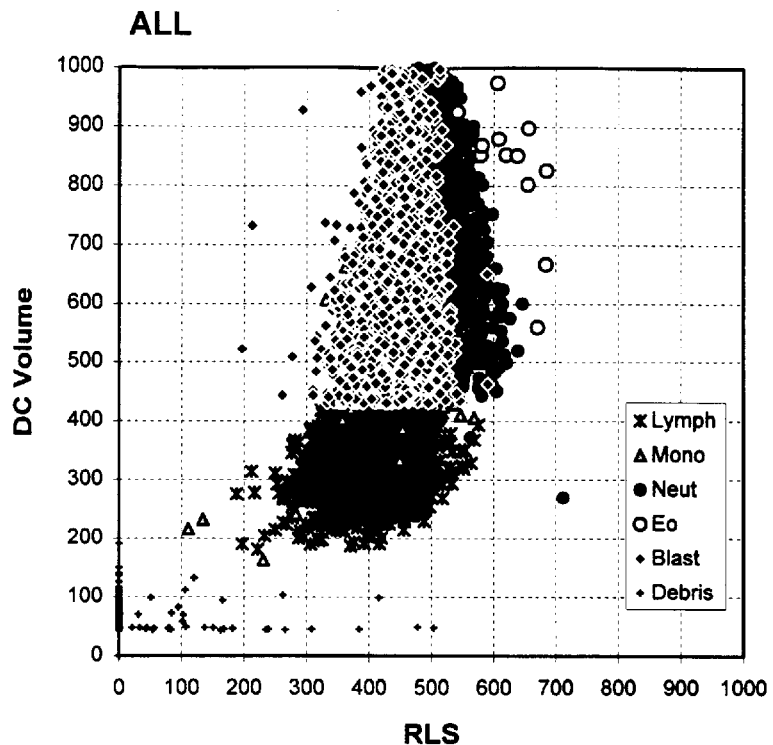
Figure 16B:
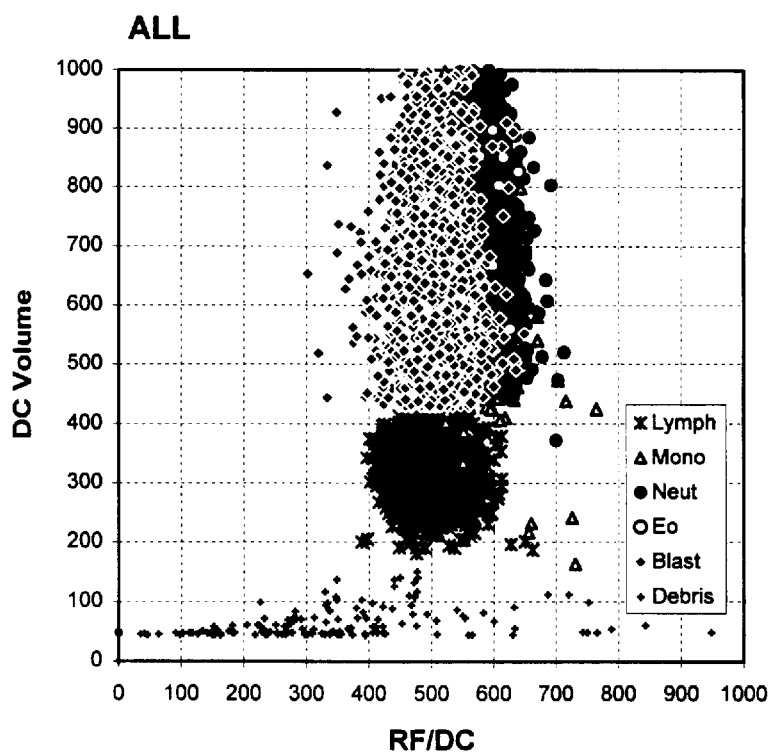
Figure 17A:
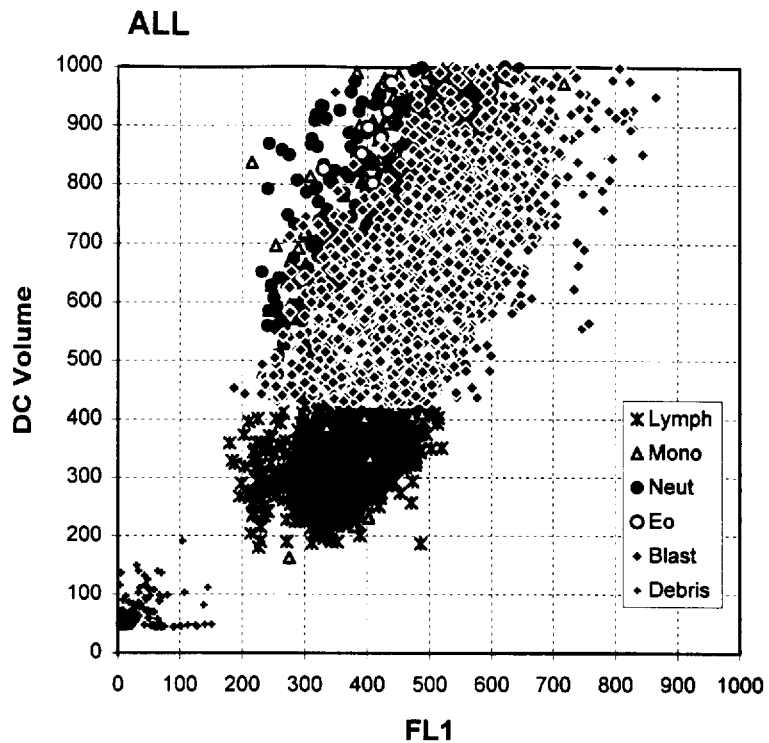
Figure 17B:
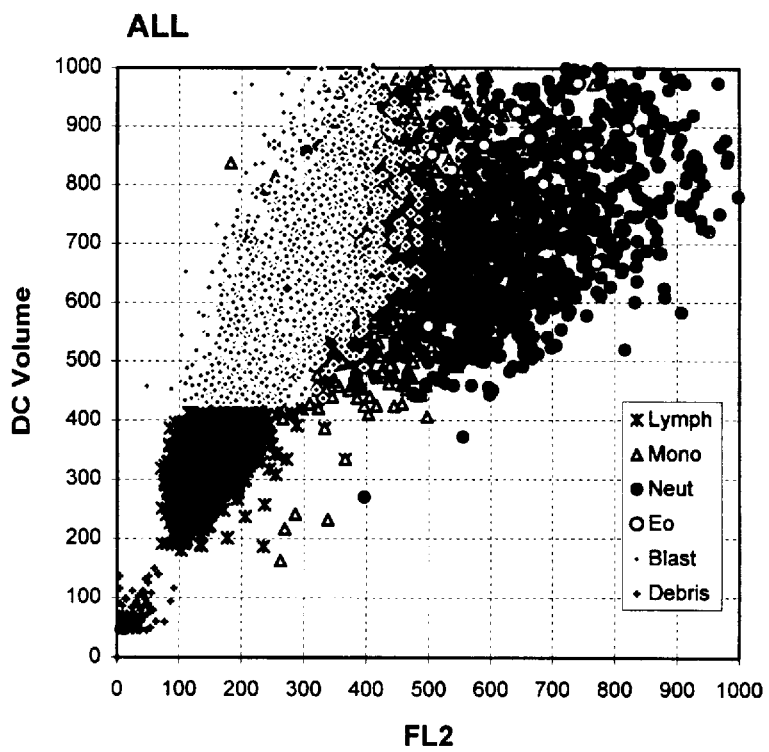
Figure 18A:
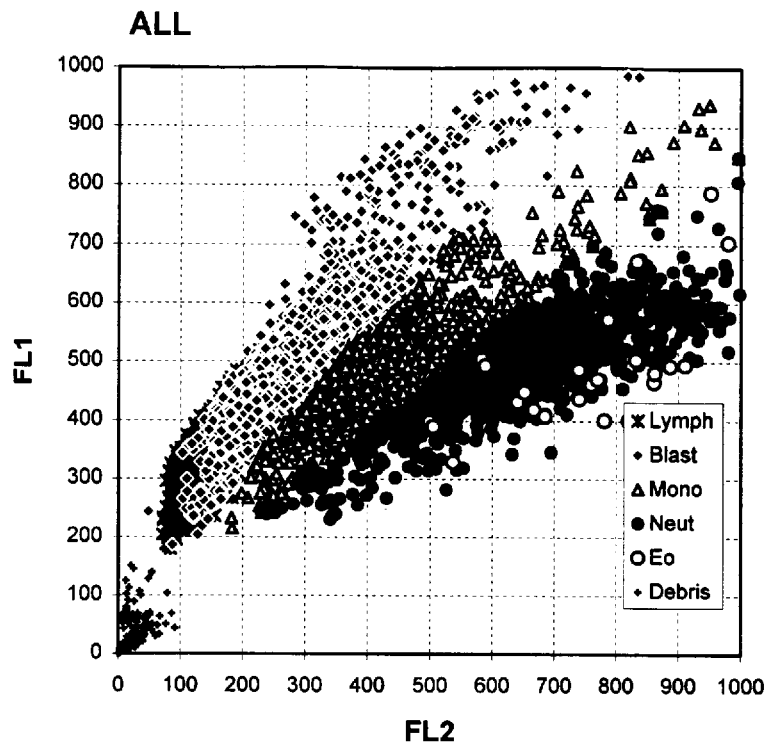
Figure 18B:
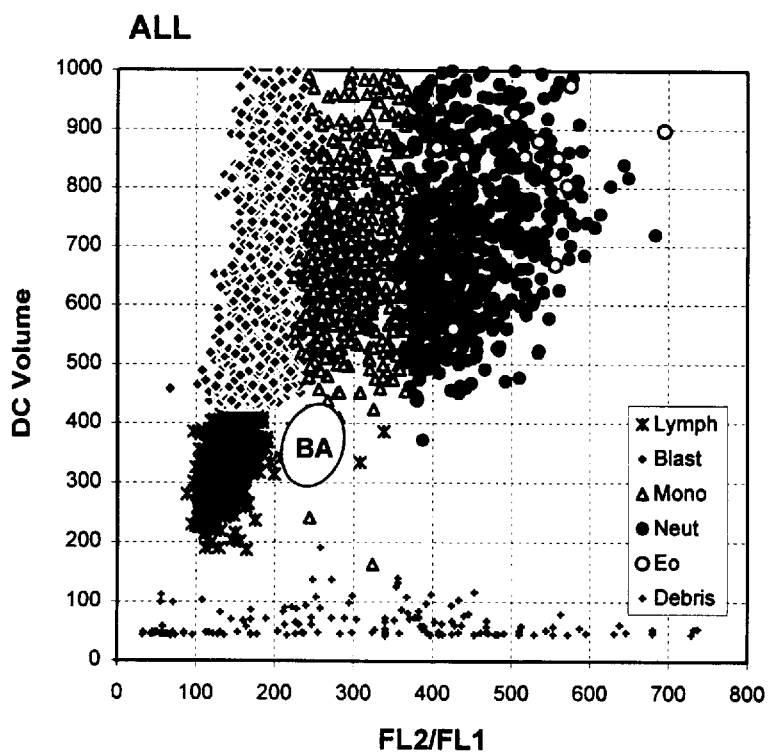

FIGS. 11A, 11B, 12A, 12B, 13A, 13B, 14A and 14B show scattergrams of various combinations of measurements for a normal peripheral blood specimen, that is, one which contains only the five normal white cell populations, lymphocytes (Lymph), monocytes (Mono), neutrophils (Neut), eosinophils (Eo) and basophils (Baso). Also shown is a cluster called Debris which contains red cell fragments, platelets and non-viable white cells, and may contain nucleated red cells (NRBC). FIG. 11A shows a DC Volume vs. LMALS scattergram. LMALS provides optimum separation of Lymph+Mono+Baso vs. Neut+Eo. FIG. 11B shows a DC vs. log UMALS scattergram. UMALS provides optimum separation of the Eo cluster. FIG. 12A shows a DC Volume vs. RLS scattergram. RLS is obtained by summing the LMALS and UMALS measurements, obtaining the log of the sum, and rotating or normalizing the result relative to the DC Volume measurement. RLS combines the discriminatory features of LMALS and UMALS. In both FIGS. 11A and 12A it is evident that the Mono cluster is separable from Lymph+Baso by DC. FIG. 12B shows a DC Volume vs. RF (conductivity)/DC (volume) scattergram with the Baso and Lymph clusters separated by RF/DC. The overlap of Baso with Neut and Eo is resolved as a result of the separation obtained with the light scatter measurements shown in FIGS. 11A–12A. FIGS. 13A and 13B show a DC Volume vs. FL2 (RNA fluorescence measured as described above) scattergram and a DC Volume vs. FL1 (DNA fluorescence measured as described above) scattergram, respectively. In these two views, the five normal populations are shown in various degrees of overlap. FIG. 14A shows a FL1 vs. FL2 scattergram. Comparing this figure with the previous two, it is evident that all five normal populations are discernable. In addition, a mostly empty region BL is identified as the location on this scattergram where blasts would be found, if the sample were to have any. FIG. 14B shows a DC vs. FL2/FL1 scattergram. The ratio of the two fluorescence measurements preserves the blast region BL and facilitates gating, or determining a boundary, for that region. FIGS. 15A–18B show scattergrams of various combinations of measurements for an abnormal acute lymphocytic leukemia (ALL) peripheral blood specimen, which contains four of the normal white cell populations, lymphocytes (Lymph), monocytes (Mono), neutrophils (Neut) and eosinophils (Eo), and a very high concentration of blasts (Blast). FIGS. 15A–16B show scattergrams of DC Volume vs. LMALS, DC Volume vs. UMALS, DC Volume vs. RLS and DC Volume vs. RF/DC, respectively. In all those figures, the Blast population overlaps with all the other clusters, making it impossible to obtain proper classification with those measurements alone. FIGS. 17A–17B show DC vs. FL1 and DC vs. FL2 scattergrams, respectively. The Blast population, in both cases, severely overlaps with the other clusters. FIG. 18A shows a FL1 vs. FL2 scattergram. In this case, most of the populations are resolved, except that the Blast cluster overlaps with the Lymph cluster. FIG. 18B shows a DC Volume vs. FL2/FL1 scattergram. Lymph, Blast, Mono and Neut are fully resolved. A region BA shows the area where basophils would be found. The Eo cluster is separable by UMALS (FIG. 15B).

Figure 19A:
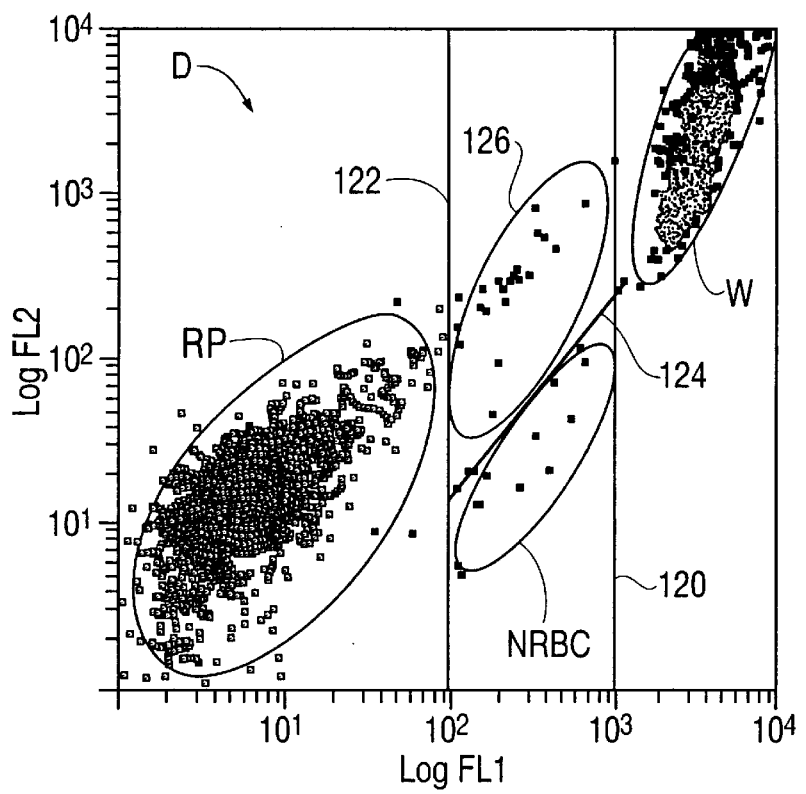
Figure 19B:
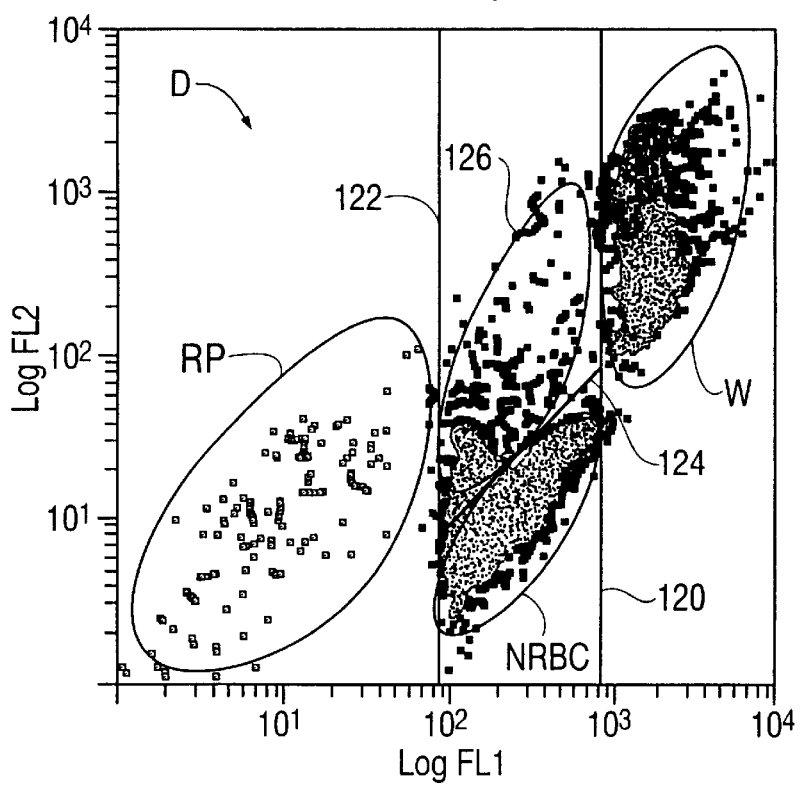
Figure 20A:
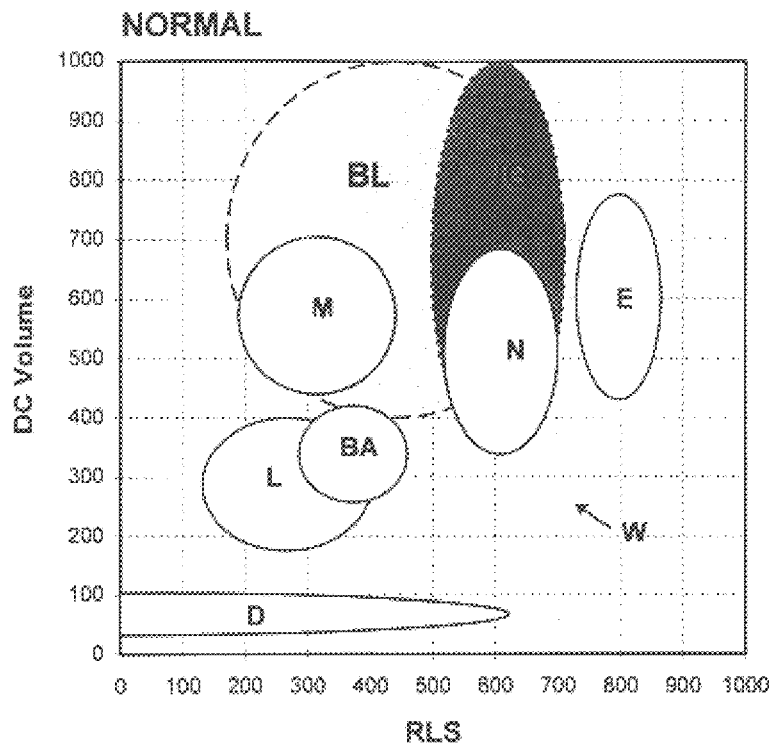
Figure 20B:
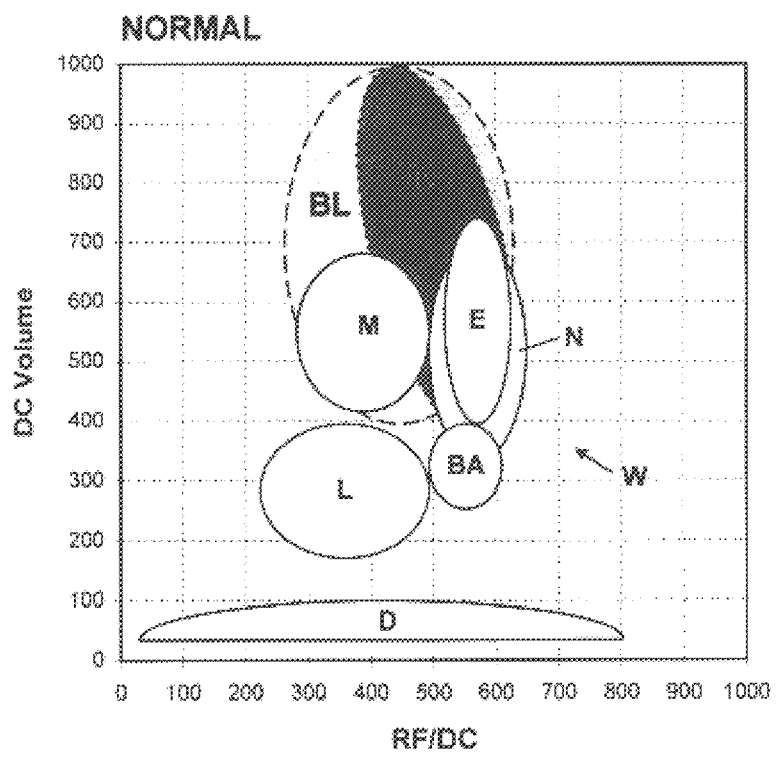
Figure 21A:
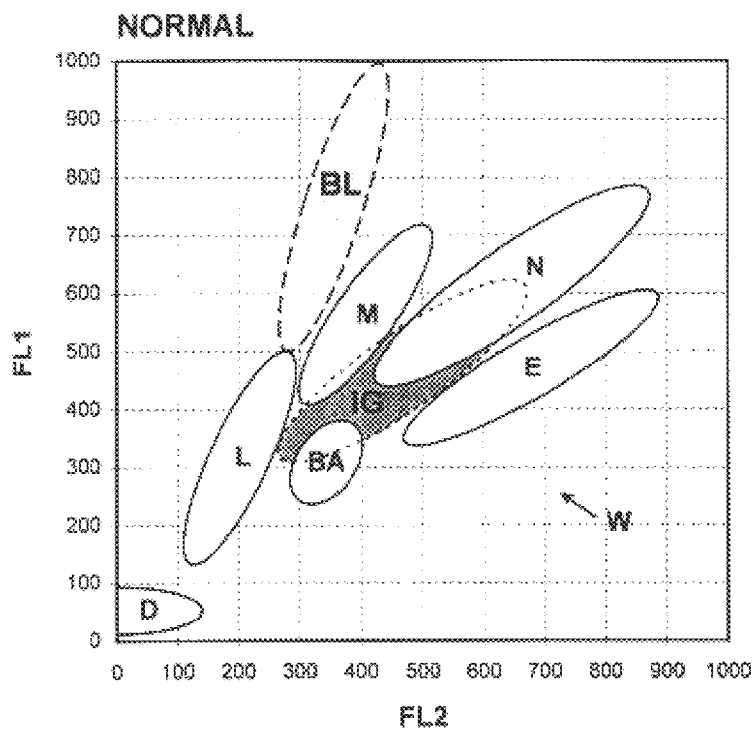
Figure 21B:
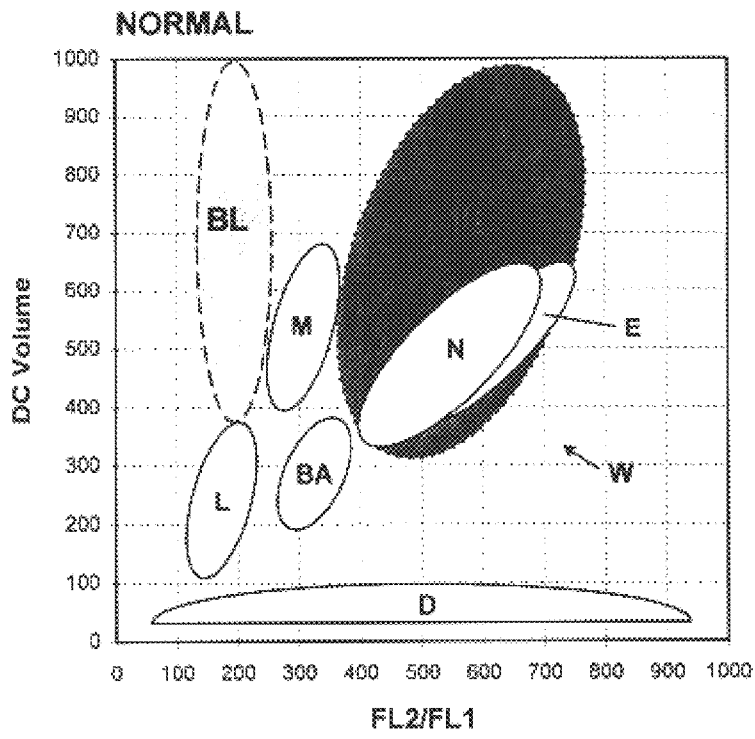

FIGS. 19A–B show Log FL2 vs. Log FL1 scattergrams for a normal blood sample and an abnormal blood sample containing nucleated red blood cells (NRBC). A cluster W contains white cells and is the equivalent of all the white cell populations shown in FIGS. 11A–18B. A set of clusters D is composed of a cluster RP, which contains red cell fragments and platelets, a cluster NRBC, which contains nucleated red blood cells, and a cluster 126 which contains non-viable white cells. The cluster set D is the equivalent of the Debris population shown in FIGS. 11A–18B. Three boundaries 120, 122, 124 define and classify the clusters comprising cluster set D. Boundary 120 separates the white cells W from the cluster set D. Boundary 122 separates the red cell fragments and platelets RP from the NRBC cluster and non-viable white cell cluster 126. Boundary 124 separates the NRBC cluster from the non-viable white cell cluster 126.

Figure 22:
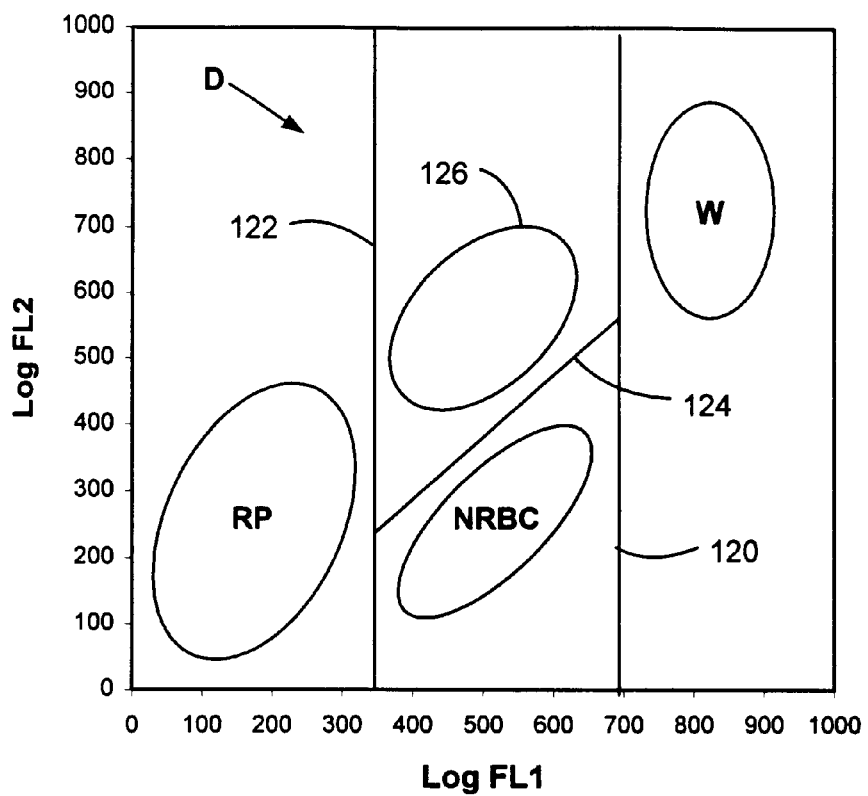

A preferred data analysis method is described as follows. Referring to FIGS. 20A–21B, DC Volume and FL1 are used to identify the debris D population from the white cells W. RLS, DC Volume, RF/DC, FL1 and FL2 are used to classify the five normal white cell populations: Neutrophils N and eosinophils E are identified with RLS; monocytes M are identified with RLS and DC Volume; lymphocytes L and basophils B are first identified as one group by RLS and DC Volume, then separated by RF/DC, FL1 and FL2. Blasts BL are identified by FL1, FL2 and DC Volume. The FL2/FL1 computed parameter provides a normalized, orthogonal view, which facilitates classification. Immature granulocytes IG are identified by measuring a significant shift to lower fluorescence level in both the FL1 and FL2 parameters, as well as a shift to higher DC Volume levels. All the aforementioned normal and abnormal white blood cell types are reported as percentages of the total white cell population, as well as absolute concentrations (LYMPH %, LYMPH#, MONO %, MONO#, NEUT %, NEUT#, EO %, EO#, BASO %, BASO#, IMMGRAN %, IMMGRAN#, BLAST %, BLAST#). Absolute total white cell count (WBC) is also reported. Referring to FIG. 22, the white cells W are identified with FL1 by boundary 120. The red cell fragments and platelets RP are identified with FL1 by boundary 122. The nucleated red blood cells NRBC and the non-viable white cells are identified with FL1 by boundaries 120, 122 and separated by boundary 124, which is a function of FL1 and FL2. Nucleated red blood cells NRBC are reported as a percent of white cells (NRBC %) and as an absolute concentration (NRBC#). If non-viable white cells 126 are present, they are reported as Fragile White Cell Fraction percentage and absolute concentration (FWCF %, FWCF#), and the absolute white cell count (WBC) is adjusted accordingly.

EXAMPLE 3

Following is described a method for obtaining an extended analysis of one or more white cell populations by labeling the cells of interest with one or more fluorochromes. In this example, lymphocytes are labeled with a cocktail of monoclonal antibodies containing CD3, CD4 and CD8, each antibody conjugated with a different fluorochrome, as shown in Table 2. Referring to FIG. 2, 34 $\mu$l of aliquot A3 is delivered to a mixing chamber MC3 in the sample prep unit 14, mixed with 10 $\mu$l of monoclonal antibody cocktail M and incubated for 30–60 seconds. Lyse and quench are added to the sample according to Table 1 in Example 2. Metering pump MP3 is used to deliver a volume of sample $S_T$ to the flow cell by the process described in Example 1. The sample is then interrogated by the flow cell, as in Example 1. In this example, the different fluorochromes of the labeled lymphocytes are excited with either of the lasers referred to Examples 1 and 2. Following is the fluorochrome configuration for this example:

TABLE 2

| Antibody | Fluorochrome | Fluorescence Wavelength | PMT | Signal |
| --- | --- | --- | --- | --- |
| CD8 | PE-CY5 | 675 nm | PMT 2 | FL2 |
| CD4 | PE | 575 nm | PMT 1 | FL1 |

PE—Phycoerythrin
PE-CY5—Phycoerythrin Cychrome 5 conjugate

Figure 23:
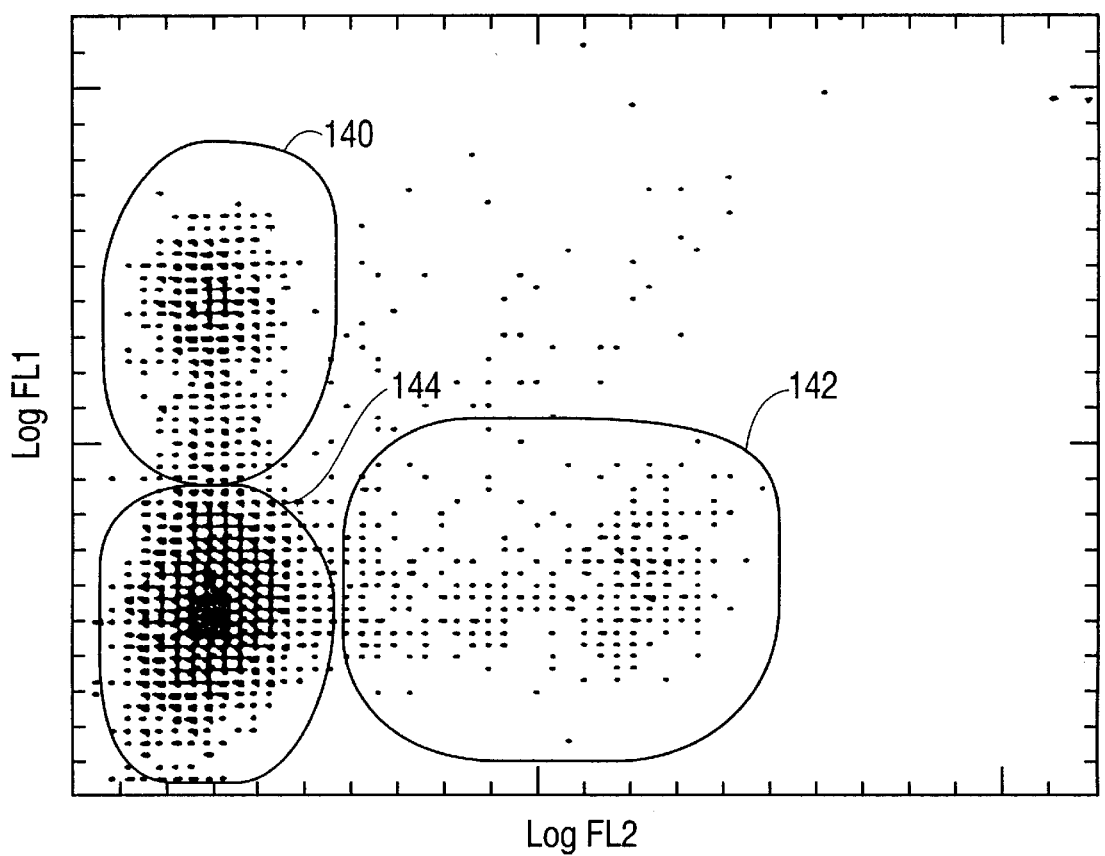

FIG. 23 shows a Log FL1 (CD4) vs. Log FL2 (CD8) scattergram. A cluster 140 contains CD4 positive lymphocytes. A second cluster 142 contains CD8 positive lymphocytes. A third cluster 144 contains lymphocytes which are neither CD4 positive nor CD8 positive, and other white cells. Referring to the VCS (Volume-Conductivity-Scatter) analysis of FIGS. 12A–B, the lymphocyte population can be isolated, or gated, such that immunofluorescence analysis can be performed and subsets can be classified and enumerated, yielding percentages relative to lymphocytes, and absolute concentration. Of particular interest is the absolute CD4 count, which is used to track the progression and treatment of HIV.

EXAMPLE 4

In the example, the above-described automated cell analyzer was used to differentiate and enumerate red cells and platelets, obtain an extended white cell differential, and obtain an extended analysis of one or more white cell populations by labeling the cells of interest with one or more fluorochromes. In this example, the sample preparations described in Examples 1–3 above are conducted simultaneously (i.e. in parallel) while the sample interrogations described in Examples 1–3 are performed sequentially. Thus, the entire analysis is conducted in a time period of about 60 seconds. The results of the three cell interrogations may be collated, but are not correlated, that is, the results of any one of the interrogations does not depend on the results of the other two interrogations. An interpretive report may be obtained by combining all of the information from the three separate interrogations to provide additional information on suspected abnormalities of the analyzed blood sample.

The invention has been described in detail while making reference to certain preferred embodiments. It will be appreciated, however, that various changes and modifications can be made without departing from the spirit of the invention and the scope literally defined by the appended claims.

What is claimed is:

1. Apparatus for differentiating and enumerating various types of blood cells in a whole blood sample, said apparatus comprising:

(a) a single flow cell comprising an optically transparent element in the form of a rectangular prism defining a passageway through which formed bodies in said sample can be made to pass one at a time, said passageway defining a cell-interrogation zone having a substantially square transverse cross-section, determined perpendicular to the direction of blood cell flow, of approximately 50 microns on each side and a length of approximately 65 microns, measured in the direction of blood cell flow;

(b) means for aspirating a sample of whole blood from a container;

(c) means for producing at least a first aliquot of the aspirated whole blood sample;

(d) means for subjecting the first aliquot of whole blood to a lysing reagent to provide a lysed sample containing predominantly white blood cells and nucleated red blood cells;

(e) means for subjecting one or more subsets of cells contained in the lysed sample to a fluorescent material, thereby causing said subsets of cells to become labeled with such fluorescent material;

(f) metering means for producing a metered volume of the lysed sample;

(g) means for causing said metered volume of said lysed sample to flow through the cell-interrogation zone of the flow cell so that blood cells in said metered volume flow through said cell-interrogation zone seriatim;

(h) circuit means for (a) simultaneously establishing DC and RF current flows through said cell-interrogation zone while blood cells are flowing therethrough, each of said blood cells being effective to (i) modulate the DC current in said zone as a function of the cell's volume, and (ii) modulate the RF current flow in said zone as a function of the cell's internal conductivity; and (b) detecting modulations in said DC and RF currents;

(i) optical means for irradiating individual blood cells flowing through said cell-interrogation zone with a beam of radiation propagating along an axis perpendicular to the direction of sample flow, said radiation being adapted to cause the fluorescent material to fluoresce;

(j) radiation scatter-detecting means for detecting radiation scattered from an irradiated blood cell in said zone;

(k) fluorescence-detecting means for detecting radiation fluorescing from a fluorescent material-labeled subset of cells as a result of being irradiated by said optical means; and (l) analyzing means, operatively coupled to said circuit means and to the respective radiation scatter- and fluorescence-detecting means, for differentiating and determining the respective concentrations of different subsets of white cells and fluorescent material-labeled cells based upon their respective DC volume (V), RF conductivity (C), light scatter (S) and fluorescence (F) properties.

2. The apparatus as defined by claim 1 wherein said means for producing at least a first aliquot is effective to produce at least a second aliquot of the aspirated whole blood sample, and said apparatus further comprises the following additional elements:

(m) means for subjecting the second aliquot of whole blood to a diluent to provide a diluted sample containing predominantly red blood cells and platelets;

(n) means for subjecting the diluted sample to a fluorescent material, whereby at least one selected subset of red cells or platelets becomes labeled with such fluorescent material; and (o) means for dispensing a metered volume of the diluted sample and causing said metered volume of said diluted sample to flow through the cell-interrogation zone of the flow cell so that blood cells in such metered volume flow through said cell-interrogation zone seriatim;

said analyzing means being effective to differentiate and determine the respective concentrations of different subsets of red blood cells and platelets based on their respective DC volume, RF conductivity, light scatter and fluorescence properties.

3. The apparatus as defined by claim 2 wherein said analyzing means is responsive to said circuit means for providing an absolute count of red blood cells in the metered volume of said diluted sample, and for providing an absolute count of white cells in the metered volume of said lysed sample.

4. The apparatus as defined by claim 1 wherein said analyzing means is effective to differentiate five different subsets of mature white cells by analyzing the combination of their respective DC volume (V), RF conductivity (C) and light scattering (S) properties.

5. The apparatus as defined by claim 1 wherein said analyzing means is effective to differentiate abnormal, immature and subsets of mature white cells based upon their respective DC volume (V), RF conductivity (C), light scatter (S) and fluorescence (F) properties.

6. The apparatus as defined by claim 1 wherein said flow cell supports a pair of electrodes, connectable to a source of electrical energy, and an optical element through which radiation emanating within the cell-interrogation zone can be optically coupled to an external photo-detector.

7. The apparatus as defined by claim 1 wherein said radiation scatter-detecting means comprises a first photo-detector adapted to detect radiation scattered within an angular range of between 10 and 70 degrees with respect to said axis.

8. The apparatus as defined by claim 7 wherein said first photo-detector is further adapted to detect radiation scattered within the angular ranges of (a) between about 10 and about 20 degrees, and (b) between about 20 and about 70 degrees, with respect to said axis.

9. The apparatus as defined by claim 1 wherein said radiation scatter-detecting means comprises a photo-detector adapted to detect radiation scattered at an angle of about 90 degrees with respect to said axis.

10. Apparatus for differentiating and enumerating various types of blood cells in a whole blood sample, said apparatus comprising:

(a) a single flow cell comprising an optically transparent element in the form of a rectangular prism defining a passageway through which formed bodies in said sample can be made to pass one at a time, said passageway defining a cell-interrogation zone having a substantially square transverse cross-section, determined perpendicular to the direction of formed body flow, of approximately 50 microns on each side and a length of approximately 65 microns, measured in the direction of formed body flow;

(b) means for aspirating a sample of whole blood from a container;

(c) means for producing at least a first aliquot of the aspirated whole blood sample;

(d) means for subjecting the first aliquot of whole blood to a diluent to provide a diluted sample containing predominantly red blood cells and platelets;

(e) means for subjecting one or more subsets of cells contained in the diluted sample to a fluorescent material, thereby causing said subsets of red blood cells or platelets to become labeled with such fluorescent material;

(f) metering means for producing a metered volume of the diluted sample;

(g) means for causing said metered volume of said diluted sample to flow through the cell-interrogation zone of the flow cell so that blood cells in said metered volume flow through said cell-interrogation zone seriatim;

(h) circuit means for (a) simultaneously establishing DC and RF current flows through said cell-interrogation zone while blood cells are flowing therethrough, each of said blood cells being effective to (i) modulate the DC current in said zone as a function of the cell's volume, and (ii) modulate the RF current flow in said zone as a function of the cell's internal conductivity; and (b) detecting modulations in said DC and RF currents;

(i) optical means for irradiating individual blood cells flowing through said cell-interrogation zone with a beam of radiation propagating along an axis perpendicular to the direction of sample flow, said radiation being adapted to cause the fluorescent material to fluoresce;

(j) radiation scatter-detecting means for detecting radiation scattered from an irradiated blood cell in said zone, said radiation scatter detecting means being adapted to detect scattered radiation within a plurality of discrete angular ranges measured with respect to said axis;

(k) fluorescence-detecting means for detecting radiation fluorescing from a fluorescent material-labeled subset of cells as a result of being irradiated by said optical means; and (l) analyzing means, operatively coupled to said circuit means and to the respective radiation scatter- and fluorescence-detecting means, for differentiating and determining the respective concentrations of different subsets of red blood cells and platelets based on their respective DC volume, RF conductivity, light scatter and fluorescence properties.

11. An automated method for determining the respective concentrations of different cell types and certain respective subsets thereof in a whole blood sample comprising the steps of:

(a) providing a flow cell adapted to simultaneously measure the respective DC volume (V), RF conductivity (C), light scattering (S) and fluorescent (F) properties of blood cells passing seriatim through an interrogation zone within said flow cell, said flow cell comprising an optically transparent element in the form of a rectangular prism defining a passageway through which blood cells in said sample can be made to pass one at a time, said passageway defining a cell-interrogation zone having a substantially square transverse cross-section, determined perpendicular to the direction of blood cell flow, of approximately 50 microns on each side and a length of approximately 65 microns, measured in the direction of blood cell flow;

(b) aspirating a sample of whole blood from a container;

(c) producing first and second aliquots of the aspirated whole blood sample;

(d) subjecting said first aliquot of whole blood to a lysing reagent to provide a lysed sample of predominantly white blood cells;

(e) subjecting said second aliquot of whole blood to a diluent to provide a diluted sample;

(f) subjecting one or more subsets of cells contained in the diluted or lysed samples to a fluorescent material, thereby causing said subsets of cells to become labeled with such fluorescent material, said fluorescent material being adapted to fluoresce when exposed to radiation of predetermined wavelength;

(g) dispensing metered volumes of said lysed and diluted samples and causing the respective metered volumes of lysed and diluted samples to flow through said interrogation zone sequentially and so that the respective blood cells in said metered volumes flow through said interrogation zone seriatim;

(h) irradiating individual blood cells flowing through said interrogation zone with a beam of radiation of said predetermined wavelength propagating along an axis while establishing DC and RF current flows through said interrogation zone, each of said blood cells being effective, while passing through said interrogation zone, to (i) modulate the DC current in said interrogation zone as a function of the cell's volume, and (ii) modulate the RF current flow in said passageway as a function of the cell's internal conductivity;

(i) detecting modulations in said DC and RF currents while detecting radiation scattered by and fluorescence emitted from an irradiated blood cell in said interrogation zone;

(j) differentiating and counting normal and mature white cells in said lysed sample based upon each cell's DC volume (V), RF conductivity(C) and light scattering (S) properties; and (k) differentiating and counting different types of red blood cells and platelets in said diluted sample based upon each cell's DC volume (V), RF conductivity (C), fluorescent label (F) and light scattering (S) properties.

12. The method as defined by claim 11 further comprising the steps of (l) producing a third aliquot of whole blood and subjecting such third aliquot to a reagent containing fluorochromes conjugated to monoclonal antibodies specific to at least one selected subset of cells in said third aliquot, whereby said selected subset of cells becomes labeled with such fluorochromes; and (m) differentiating and counting such selected subset based on the V, C, S, and F properties of such subset.

13. The method as defined by claim 11 further comprising the step of differentiating and counting nucleated red blood cells, blast cells and immature cells in said lysed sample based on the respective light scattering characteristics and fluorescence of such cells.

14. The method as defined by claim 11 further comprising the step of differentiating and counting nucleated red blood cells, blast cells and immature cells in said lysed sample based on the respective light scattering characteristics and DC volume of such cells.

15. The method as defined by claim 11 wherein said lysing reagent contains said fluorescent material.

16. The method as defined by claim 15 wherein said fluorescent material comprises Coriphosphine O.

17. The method as defined by claim 11 wherein said diluent contains said fluorescent material.

18. The method as defined by claim 11 wherein said first aliquot is subjected to said fluorescent material before subjecting it to said lysing reagent.

19. The method as defined by claim 18 wherein said fluorescent material is Coriphosphine O.

20. An automated method for determining the respective concentrations of different cell types and certain respective subsets thereof in a whole blood sample comprising the steps of:

(a) providing a flow cell adapted to simultaneously measure the respective DC volume (V), RF conductivity (C), light scattering (S) and fluoresent (F) properties of blood cells passing seriatim through an interrogation zone within said flow cell, said flow cell comprising an optically transparent element in the form of a rectangular prism defining a passageway through which blood cells in said sample can be made to pass one at a time, said passageway defining a cell-interrogation zone having a substantially square transverse cross-section, determined perpendicular to the direction of blood cell flow, of approximately 50 microns on each side and a length of approximately 65 microns, measured in the direction of bold cell flow;

(b) aspirating a sample of whole blood from a container;

(c) producing an aliquot of the aspirated whole blood sample;

(d) subjecting said aliquot of whole blood to a lysing reagent to provide a lysed sample of prediminantly white blood cells;

(e) subjecting one or more subsets of cells contained in said lysed sample to a fluorescent material, thereby causing said subsets of cells to become labeled with such fluorescent material, said fluorescent material being adapted to fluoresce when exposed to radiation of predetermined wavelength;

(f) dispensing a metered volume of said lysed sample and causing the metered volume of said lysed sample to flow through said interrogation zone sequentially and so that the respective blood cells in said metered volume flow through said interrogation zone seriatim;

(g) irradiating individual blood cells flowing through said interrogation zone with a beam of radiation of said predetermined wavelength propagating along an axis while establishing DC and RF current flows through said interrogation zone, each of said blood cells beiing effective, while passing through said interrogation zone, to (i) modulate the DC current in said interrogation zone as a function of the cell's volume, and (ii) modulate the RF current flow in said passageway as a function of the cell's internal conductivity;

(h) detecting modulations in said DC and RF currents while detecting radiation scattered by and fluorescence emitted from an irradiated blood cell in said interrogation zone;

(i) differentiating and counting different subsets of mature white cells in said lysed sample based upon each cell's DC volume (V), RF conductivity (C) and light scattering (S) properties; and (j) differentiating and counting different subsets of white cells labeled with fluoresent material based upon each cell's DC volume (V), RF conductivity (C), fluorescent label (F) and light scattering (S) properties.

21. An automated method for determining the respective concentrations of different cell types and certain respective subsets thereof in a whole blood sample comprising the steps of:

(a) providing a flow cell adapted to simultaneously measure the respective DC volume (V), RF conductivity (C), light scattering (S) and fluorescent (F) properties of blood cells passing seriatim through an interrogation zone within said flow cell, said flow cell comprising an optically transparent element in the form of a rectangular prism defining a passageway through which blood cells in said sample can be made to pass one at a time, said passageway defining a cell-interrogation zone having a substantially square transverse cross-section, determined perpendicular to the direction of blood cell flow, of approximately 50 microns on each side and a length of approximately 65 microns, measured in the direction of blood cell flow;

(b) aspirating a sample of whole blood from a container;

(c) producing an aliquot of the aspirated whole blood sample;

(d) subjecting said aliquot of whole blood to a diluent to provide a diluted sample of predominantly red blood cells, white blood cells and platelets;

(e) subjecting one or more subsets of cells contained in said diluted sample to a fluorescent material, thereby causing said subsets of cells to become labeled with such fluorescent material, said fluorescent material being adapted to fluoresce when exposed to radiation of predetermined wavelength;

(f) dispensing a metered volume of said diluted sample and causing the metered volume of said diluted sample to flow through said interrogation zone so that the respective blood cells in said metered volume flow through said interrogation zone seriatim;

(g) irradiating individual blood cells flowing through said interrogation zone with a beam of radiation of said predetermined wavelength propagating along an axis while establishing DC and RF current flows through said interrogation zone, each of said blood cells being effective, while passing through said interrogation zone, to (i) modulate the DC current in said interrogation zone as a function of the cell's volume, and (ii) modulate the RF current flow in said passageway as a function of the cell's internal conductivity;

(h) detecting modulations in said DC and RF currents while detecting radiation scattered by and fluorescence emitted from an irradiated blood cell in said interrogation zone;

(i) differentiating and counting red blood cells, white blood cells and platelets in said diluted sample based upon each cell's DC volume (V), RF conductivity (C) and light scatter (S); and (j) differentiating and counting different subsets of red cells, white cells and platelets labeled with fluorescent material based upon each cell's DC volume (V), RF conductivity (C), fluorescent label (F) and light scattering (S) properties.

22. The method as defined by claim 21 wherein said diluent comprises phosphate buffered saline, Coriphosphine-O (CPO), dodecyl-β-D-maltose and Proclin 300.

23. The method as defined by claim 22 further comprising the steps of determining the hemoglobin content of each red blood cell on the basis of its respective DC volume and light scattering properties.

24. The method as defined by claim 22 further comprising the step of analyzing the hemoglobin content of each reticulated red blood cell as the basis of its respective DC volume, light scattering and fluorescence characteristics.

* * * * *